United States Patent [19]
Trova et al.

[11] Patent Number: 5,914,327
[45] Date of Patent: Jun. 22, 1999

[54] BIARYL-PYRIDOQUINAZOLINONE DERIVATIVES AS ANTI-CANCER AGENTS

[75] Inventors: Michael P. Trova, Schenectady; Nan Zhang, Valley Cottage; Douglas B. Kitchen, Schenectady, all of N.Y.

[73] Assignee: American Cyanamid Company, Madison, N.J.

[21] Appl. No.: 08/965,552

[22] Filed: Nov. 6, 1997

Related U.S. Application Data

[60] Provisional application No. 60/032,050, Nov. 26, 1996.
[51] Int. Cl.$^6$ ............... A61K 31/505; A61K 31/55; C07D 471/04
[52] U.S. Cl. ............... 514/212; 514/267; 544/252; 540/600
[58] Field of Search ............... 544/252; 514/267, 514/212; 540/600

[56] References Cited

U.S. PATENT DOCUMENTS

| | | |
|---|---|---|
| 4,033,961 | 7/1977 | Schwender et al. . |
| 4,104,389 | 8/1978 | Schwender et al. . |
| 4,348,396 | 9/1982 | Kierstead et al. . |
| 4,551,460 | 11/1985 | Tilley ........................... 544/252 |

OTHER PUBLICATIONS

Denny et al., Structure–activity relationships for the mutagenic acitivity of tricyclic intercalating agents in *Selmonella typhimurium*, Mutation Research, 232 (1990) p. 233.

Ebeid et al., Synthesis and Antitumor Activity of Some N(p–Substituted Sulfamoyl–phenyl) Acridone–4–Carboxamides and N(p–substituted Sulfamoylphenyl)–11–oxo–11 H–Pyrido[2,1–b] Quinazoline–6–Carboxamides, Egypt. J. Pharm Sci., vol.33, No. 1–2, pp. 293–303 (1992).

*Primary Examiner*—Emily Bernhardt
*Attorney, Agent, or Firm*—Arnold S. Milowsky

[57] ABSTRACT

This invention provides a compound having the formula:

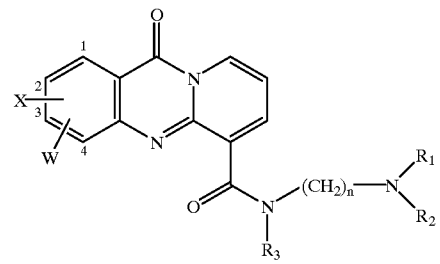

wherein:
(A) n=2–4;
(B) $R_1$ and $R_2$ are the same or different and selected from the group consisting of H, $(C_1-C_3)$alkyl, —$CH_2CH_2OH$, —$CH_2CH_2NH_2$, and —$CH_2CH_2N(CH_3)_2$ or $R_1$ and $R_2$ are alkyl moieties which may taken together to form a 4- to 7-membered ring;
(C) $R_3$ is selected from H, —$CH_3$, —$CH_2CH_3$, —$CH_2CH_2NH_2$;
(D) X is located at the 2-, or 3-position and is selected from the group consisting of 2-naphthyl, 1-naphthyl, 1-phenanthrenyl, 2-phenanthrenyl, 3-phenanthrenyl, 4-phenanthrenyl, 9-phenanthrenyl, phenyl, and mono- or polysubstituted phenyl wherein the substituents are selected from the group consisting of —$OR_4$, —$NR_5R_6$, $(C_1-C_3)$ alkyl, —$CF_3$, F, Cl, Br, I, —$NO_2$, —CN, —$SO_3H$, —$SO_2NR_5R_6$, —$CO_2H$, —$CO_2R_4$, and phenyl;
$R_4$ is H or $(C_1-C_4)$alkyl;
$R_5$ and $R_6$ are the same or different and are selected from H, or $(C_1-C_4)$alkyl, or $R_5$ and $R_6$ are alkyl groups which may be taken together to form a 4–7 membered ring;
(E) W is selected from H, —$OR_4$, —$NR_5R_6$, $(C_1-C_3)$ alkyl, —$CF_3$, F, Cl, Br, I, —$NO_2$, —CN, —$SO_2NR_5R_6$, —$CO_2R_4$; or a pharmacologically acceptable salt thereof which is useful as an antineoplastic agent.

18 Claims, No Drawings

BIARYL-PYRIDOQUINAZOLINONE DERIVATIVES AS ANTI-CANCER AGENTS

BACKGROUND OF THE INVENTION

This application claims the benefit of U.S. Provisional Application No. 60/032,050, filed Nov. 26, 1996.

Most of DNA intercalating anti-tumor drugs have a common structure: a tri- or tetracyclic chromophore with one or two flexible side chains. Denny et al. reported synthesis and biological activity of N-[2-(dimethylamino)ethyl]-11-oxo-11H-pyrido[2,1-b]quinalzoline-6-carboxamide (I) as a potential anti-cancer agent [Mutation Research 232: 233 (1990)]. In these reports, they claim that this compound showed some in vitro activity and mutagenic activity, but was inactive in a P388 mouse model. Ebeid et. al. reported synthesis of N(p-substituted sulfamoylphenyl)-11-oxo-11H-pyrido[2,1-b]quinalzoline-6-carboxamides (II). Only one compound showed in vitro activity. [Egypt. J. Pharm. Sci. 33: 293 (1992)].

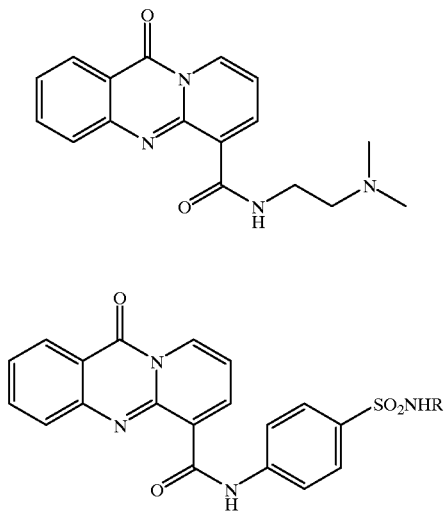

I

II

Substituted 11-oxo-11H-pyrido[2,1-b]quinalzolines have been patented as anti allergy agents. Neither these patents nor the references cited above, cover any biaryl compounds described in this application. [U.S. Pat. Nos. 4,033,961, 4,104,389, and 4,384,396].

BRIEF SUMMARY OF THE INVENTION

This invention provides compounds having the formula:

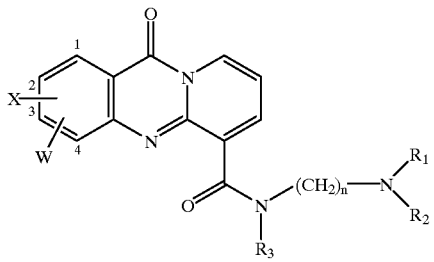

wherein:
(A) n=2–4;
(B) $R_1$ and $R_2$ are the same or different and selected from the group consisting of H, $(C_1-C_3)$alkyl, $—CH_2CH_2OH$, $—CH_2CH_2NH_2$, and $—CH_2CH_2N(CH_3)_2$ or $R_1$ and $R_2$ are alkyl moieties which may taken together to form a 4 to 7-membered ring;
(C) $R_3$ is selected from H, $—CH_3$, $—CH_2CH_3$, $—CH_2CH_2NH_2$;
(D) X is located at the 2-, or 3-position and is selected from the group consisting of 2-naphthyl, 1-naphthyl, 1-phenanthrenyl, 2-phenanthrenyl, 3-phenanthrenyl, 4-phenanthrenyl, 9-phenanthrenyl, phenyl, and mono- or polysubstituted phenyl wherein the substituents are selected from the group consisting of $—OR_4$, $—NR_5R_6$, $(C_1-C_3)$ alkyl, $—CF_3$, F, Cl, Br, I, $—NO_2$, $—CN$, $—SO_3H$, $—SO_2NR_5R_6$, $—CO_2H$, $—CO_2R_4$, and phenyl;
$R_4$ is H or $(C_1-C_4)$alkyl;
$R_5$ and $R_6$ are the same or different and are selected from H, or $(C_1-C_4)$alkyl, or $R_5$ and $R_6$ are alkyl groups which may be taken together to form a 4–7 membered ring;
(E) W is selected from H, $—OR_4$, $—NR_5R_6$, $(C_1-C_3)$ alkyl, $—CF_3$, F, Cl, Br, I, $—NO_2$, $—CN$, $—SO_2NR_5R_6$, $—CO_2R_4$; or a pharmaceutically acceptable salt thereof.

A more preferred embodiment of the present invention is provided by compounds having the formula:

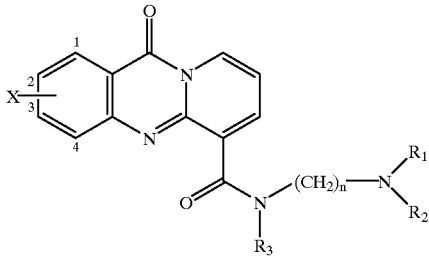

wherein:
(A) n=2–4;
(B) $R_1$ and $R_2$ are the same or different and selected from the group consisting of H, $(C_1-C_3)$alkyl, $—CH_2CH_2OH$, $—CH_2CH_2NH_2$, and $—CH_2CH_2N(CH_3)_2$ or $R_1$ and $R_2$ are alkyl moieties which may taken together to form a 4- to 7-membered ring;
(C) $R_3$ is selected from H, $—CH_3$, $—CH_2CH_3$, $—CH_2CH_2NH_2$;
(D) X is located at the 2-, or 3-position and is selected from the group consisting of 2-naphthyl, 1-naphthyl, 1-phenanthrenyl, 2-phenanthrenyl, 3-phenanthrenyl, 4-phenanthrenyl, 9-phenanthrenyl, phenyl, and mono- or polysubstituted phenyl wherein the substituents are selected from the group consisting of $—OR_4$, $—NR_5R_6$, $(C_1-C_3)$ alkyl, $—CF_3$, F, Cl, Br, I, $—NO_2$, $—CN$, $—SO_3H$, $—SO_2NR_5R_6$, $—CO_2H$, $—CO_2R_4$, and phenyl;
$R_4$ is H or $(C_1-C_4)$alkyl;
$R_5$ and $R_6$ are the same or different and are selected from H, or $(C_1-C_4)$alkyl, or $R_5$ and $R_6$ are alkyl groups which may be taken together to form a 4–7 membered ring; or a pharmaceutically acceptable salt thereof.

DETAILED DESCRIPTION OF THE INVENTION

The preparation of compounds encompassed by formula 7 is described below in Flowsheet A wherein n, $R_1$, $R_2$, $R_3$, and X are as described above. 2-Amino-5-iodobenzoic acid (2) can be prepared by iodination of anthranilic acid. [Klemme, C. J., J. Org. Chem. 5: 227 (1940)]. Condensation of 2-amino-5-iodobenzoic acid (2) with 2-chloronicotinic acid (3) in a polar protic solvent such as ethanol or aqueous ethanol in the presence of a catalytic amount of a mineral acid such as hydrochloric acid at temperatures in excess of 80° C. provides heterocycle 4. The carboxylic acid group within 4 can be converted into an amide 6 by reaction with amine 5 in the presence of a coupling agent, such as benzotriazol-1-yloxytris(dimethylamino)phosphonium hexafluorophosphate (BOP reagent), a base, such as N,N-diisopropylethylamine (Hünigs base) in an inert solvent such as dichloromethane. In some cases, mixtures of regioisomeric amides are formed from which the desired amide can be isolated by chromatography, distillation, or recrystallization. Compound 1 is prepared by a palladium (0) mediated coupling reaction of 6 with arylboronic acid a, a catalytic amount of palladium (0), such as tetrakis(triphenylphosphine)palladium (0) (Pd(PPh$_3$)$_4$), a base such as sodium carbonate, in water, and an inert solvent such as toluene at or below reflux temperature.

An alternative approach to prepare amide 6, involves first transformation of acid 4 into its acid chloride 9 by reaction of 4 with oxalyl chloride, a catalytic amount of dimethylformamide, in an inert solvent such as dichloromethane. Acid chloride 9 is reacted with amine 5 in the presence of a base, such as triethylamine in an inert solvent, such as dichloromethane to give amide 6. In some cases, mixtures of regioisomeric amides are formed from which the desired amide can be isolated by chromatography, distillation, or recrystallization.

An alternative approach to compound 7 is reaction of iodide 6 with aryltin derivatives 10 in the presence of palladium (0), such as tetrakis(triphenylphosphine) palladium (0), in an inert solvent such as toluene, at or below the reflux temperature.

Flowsheet A

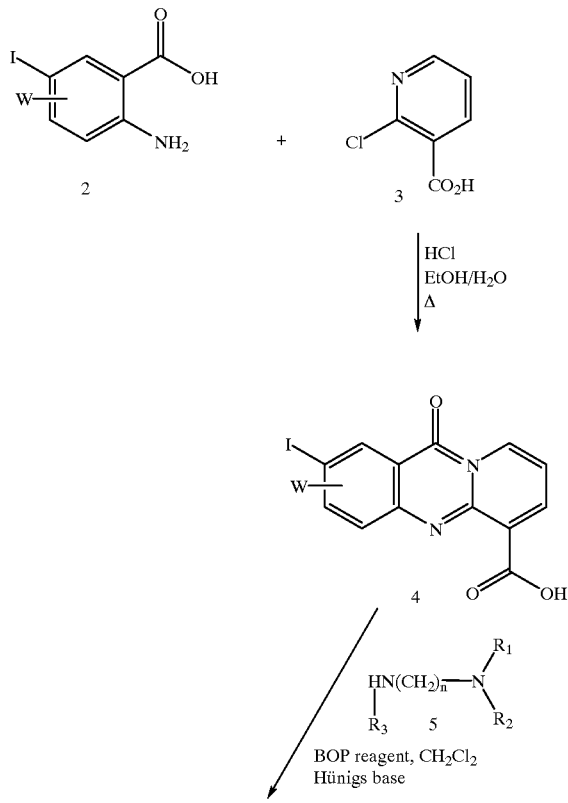

-continued
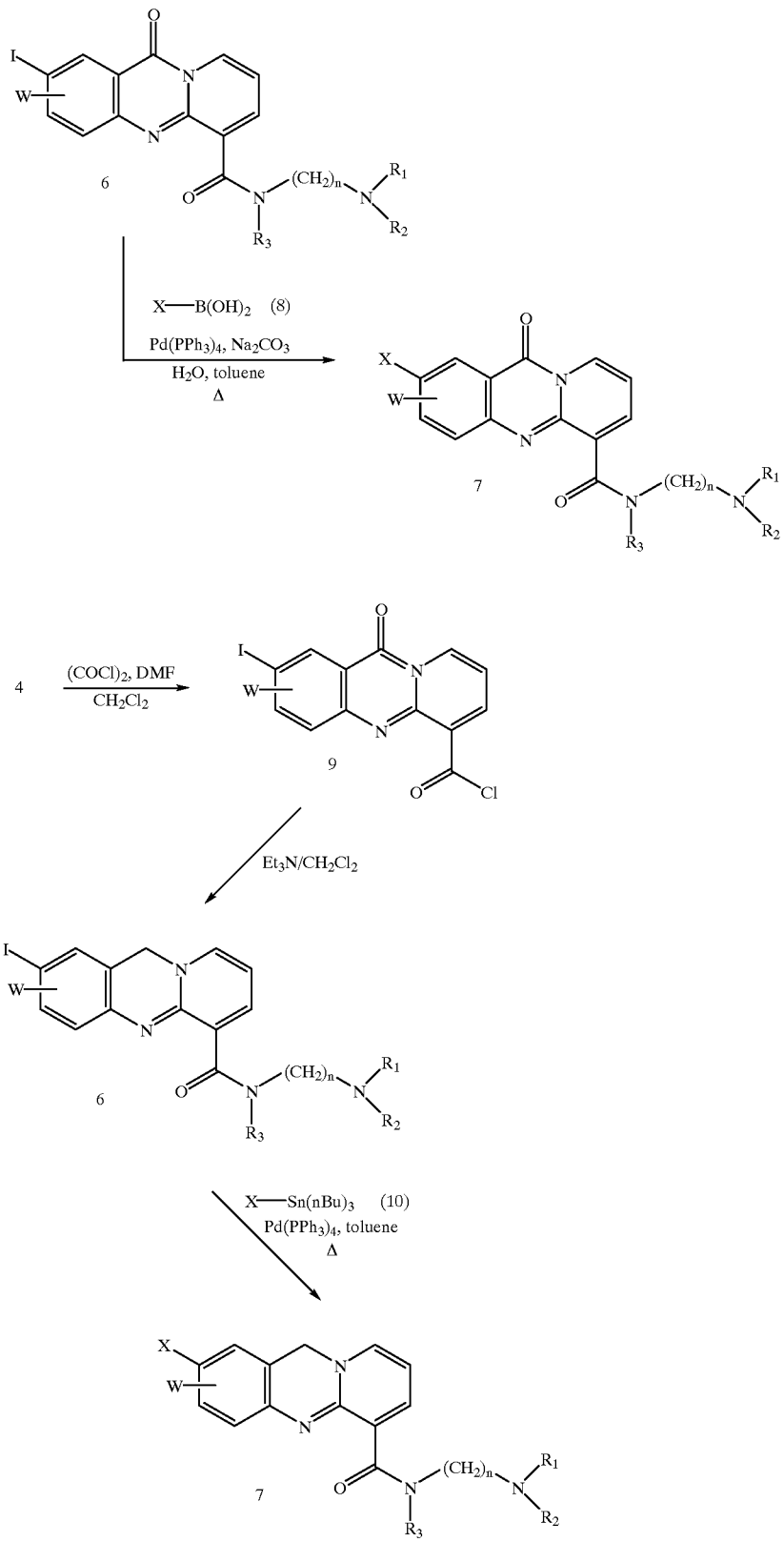

In order to avoid preparation of regioisomeric mixtures of various amides of the present invention, one can utilize protected forms of amines and alcohols as shown below in Flowsheets B–E. The preparations described in Flowsheets B–E are representative and are not inclusive, and can be applied to any carboxylic acid 4 independent of the location of the halogen atom.

Carboxylic acid 4 is reacted with amine 11, in the presence of a coupling agent, such as the BOP reagent, a base, such as Hünigs base, in an inert solvent such as dichloromethane to give amide 12 wherein n and X are as defined hereinabove, m is 0–4 as described below in Flowsheet B. Amide 12 is allowed to undergo palladium (0) mediated coupling as described hereinabove in Flowsheet A to give biaryl 13. Deprotection of 13 is effected by reaction of 13 with an acid, such as hydrochloric acid or trifluoroacetic acid in an appropriate solvent to give compound 14.

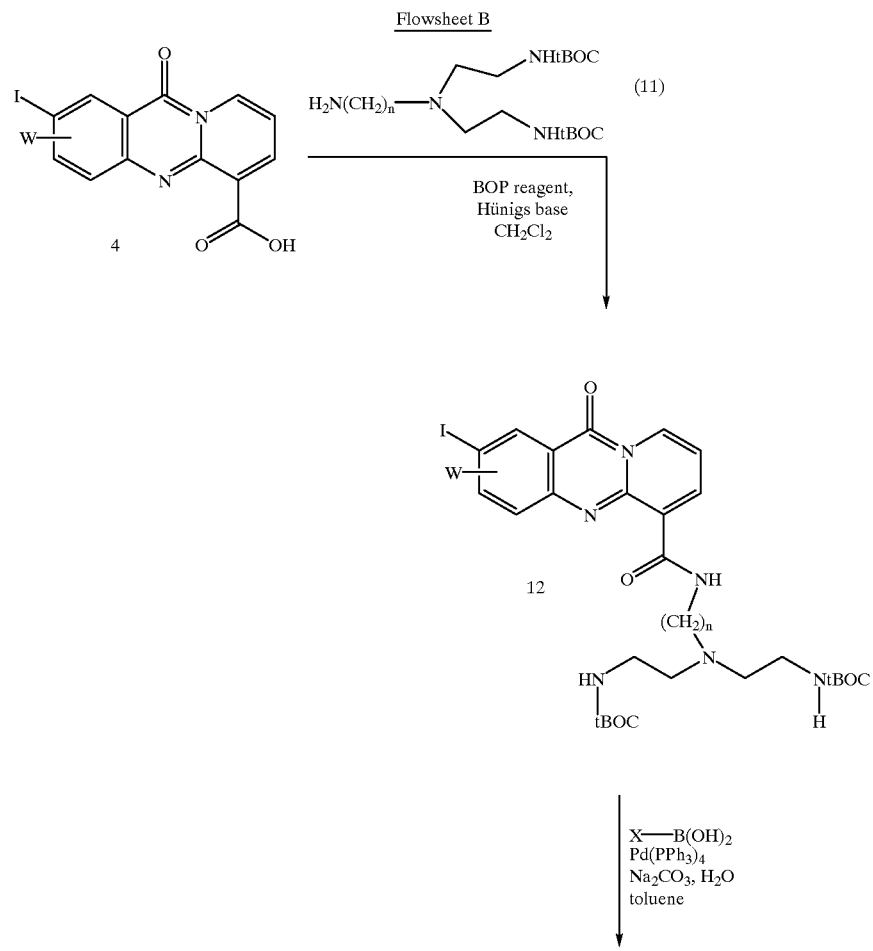

Flowsheet B

-continued

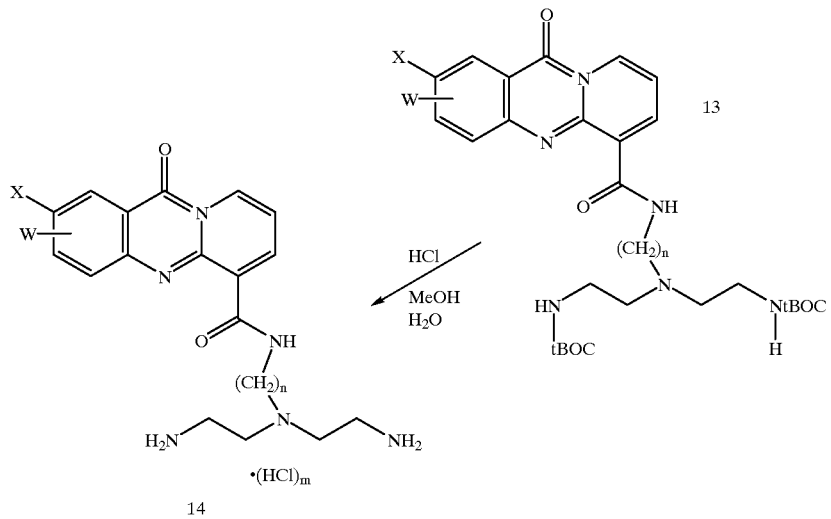

The preparation of compounds of this invention encompassed by Formula 18 is described hereinbelow in Flowsheet C wherein n and X are described above, and m is 0–4. Carboxylic acid 4 is reacted with amine 15 in the presence of a coupling agent, such as the BOP reagent, a base, such as Hünigs base, and an inert solvent such as dichloromethane to give amide 16. Amide 16 is allowed to undergo palladium (0) mediated coupling as described hereinabove in Flowsheet A to give compound 17. Deprotection of 17 is effected by reaction of 17 with an acid, such as hydrochloric acid or trifluoroacetic acid in an appropriate solvent to give compound 18.

Flowsheet C

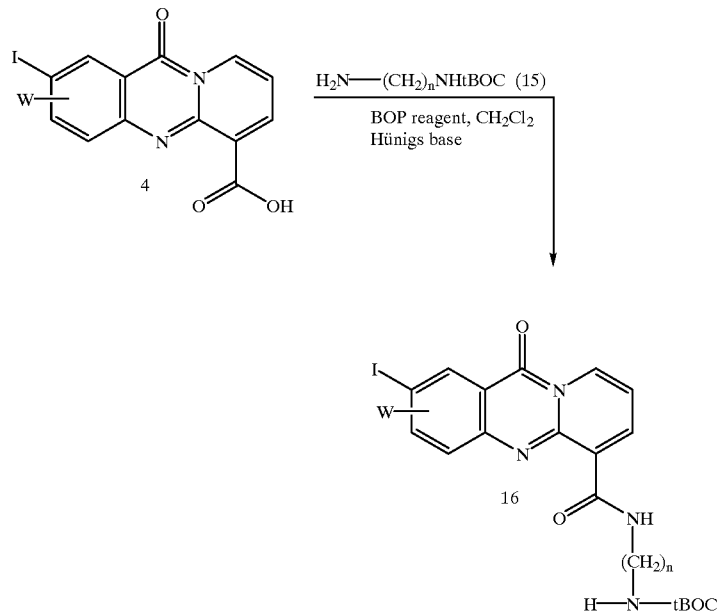

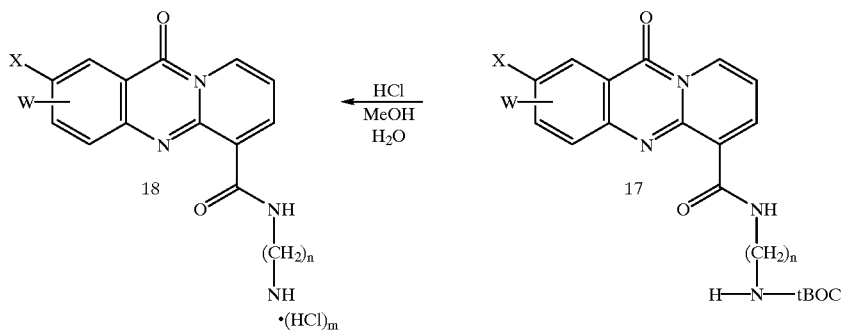

The preparation of compounds of this invention encompassed by Formula 22 is described below in Flowsheet D wherein n, W, and X are as described above, m is 0–4. Carboxylic acid 4 is reacted with amine 19 in the presence of a coupling agent, such as the BOP reagent, a base, such as Hünigs base, and an inert solvent such as dichloromethane to give amide 20. Amide 20 is allowed to undergo palladium (0) mediated coupling as described hereinabove in Flowsheet A to give biaryl 21. Deprotection of 21 is effected by reaction of 21 with an acid, such as hydrochloric acid or trifluoroacetic acid in an appropriate solvent to give compound 22.

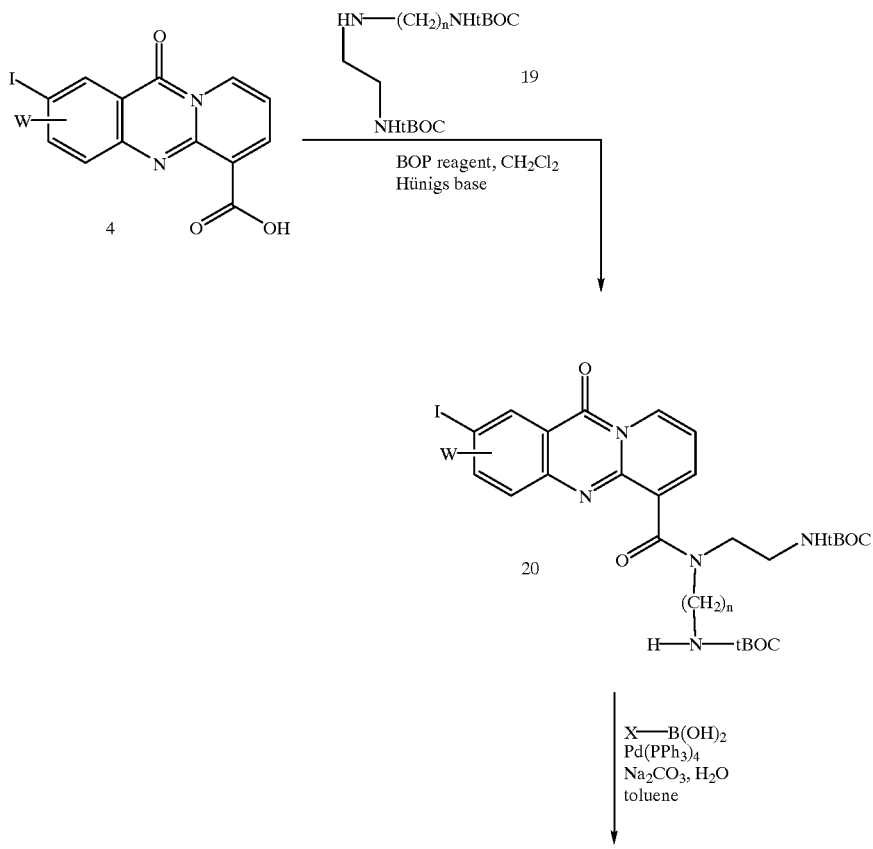

Flowsheet D

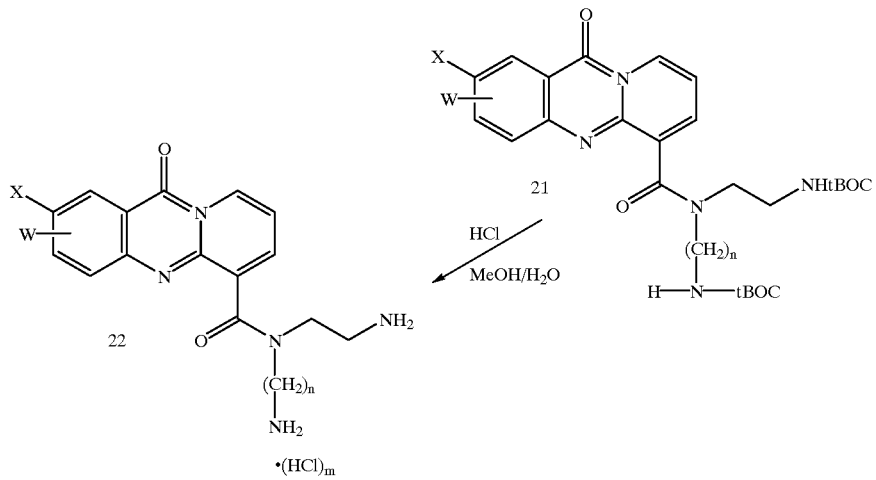

The preparation of compounds of this invention encompassed by Formula 26 is described hereinbelow in Flowsheet E wherein n, W, and X are described hereinabove, and m is 0–4. Carboxylic acid 4 is reacted with amine 23 in the presence of a coupling agent, such as the BOP reagent, a base, such as Hüinig's base, in an inert solvent such as dichloromethane to give amide 24. Amide 24 is allowed to undergo palladium (0) mediated coupling as described hereinabove in Flowsheet A to give compound 25. Deprotection of 25 is effected by reaction of 25 with an acid, such as hydrochloric acid in an appropriate solvent to give compound 26.

Flowsheet E

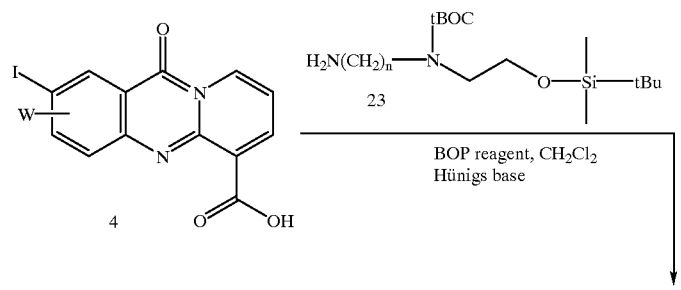

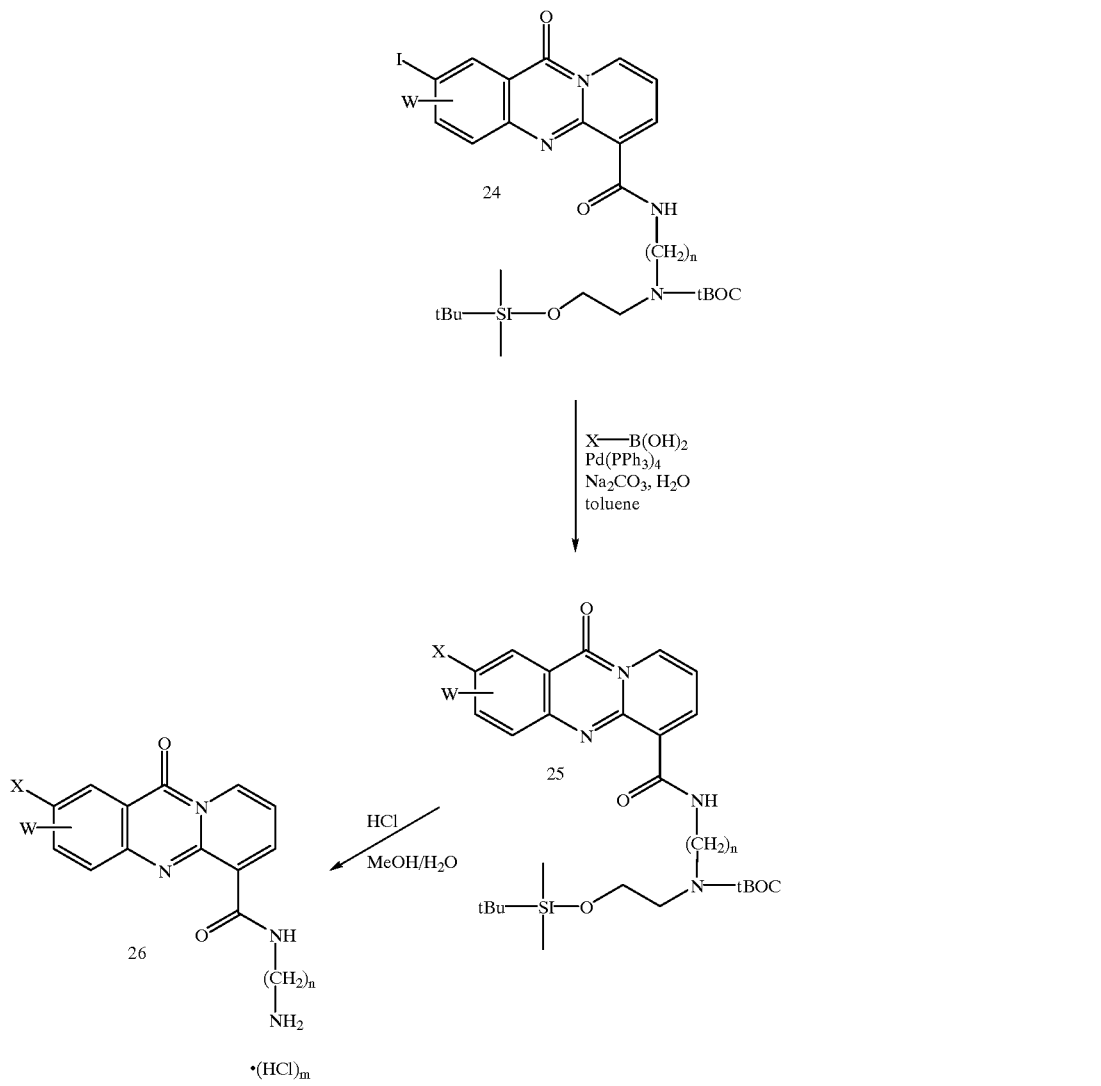

The preparation of compounds of this invention encompassed by Formulae 15, 19, 11 and 23 are described hereinbelow in Flowsheet F wherein n is described hereinabove. Diamine 27 is reacted with di-tert-butyl dicarbonate ((tBOC)₂O) in an inert solvent, such as tetrahydrofuran (THF) to provide mono-protected diamine 15.

Triamine 28 is allowed to undergo reaction with 2-(tert-butoxycarbonyloxyimino)-2-phenyl-acetonitrile (BOC—ON reagent) in the presence of a base, such as triethylamine (NEt₃), in an inert solvent such as tetrahydrofuran to give diprotected triamine 19.

Tetramine 29 is allowed to undergo reaction with the BOC—ON reagent in the presence of a base, such as triethylamine (NEt₃), in an inert solvent such as THF to give diprotected tetramine 11.

Flowsheet F

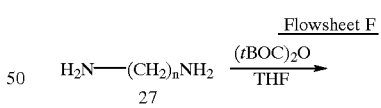

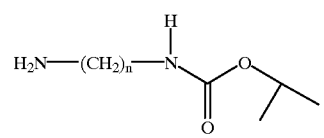

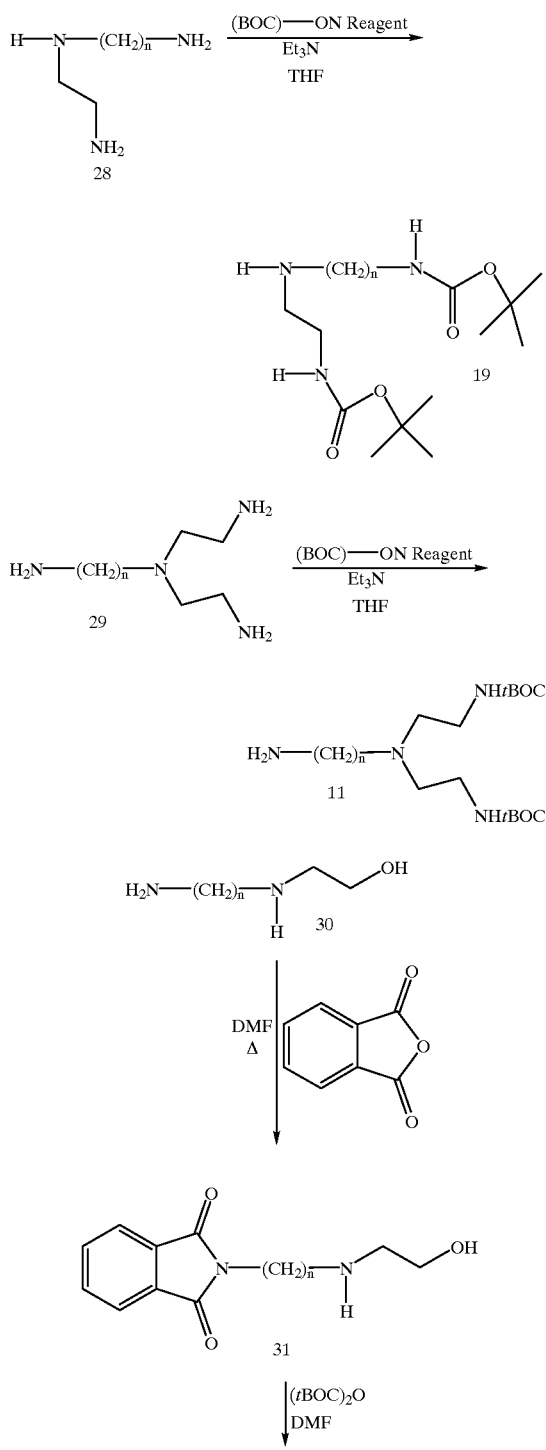

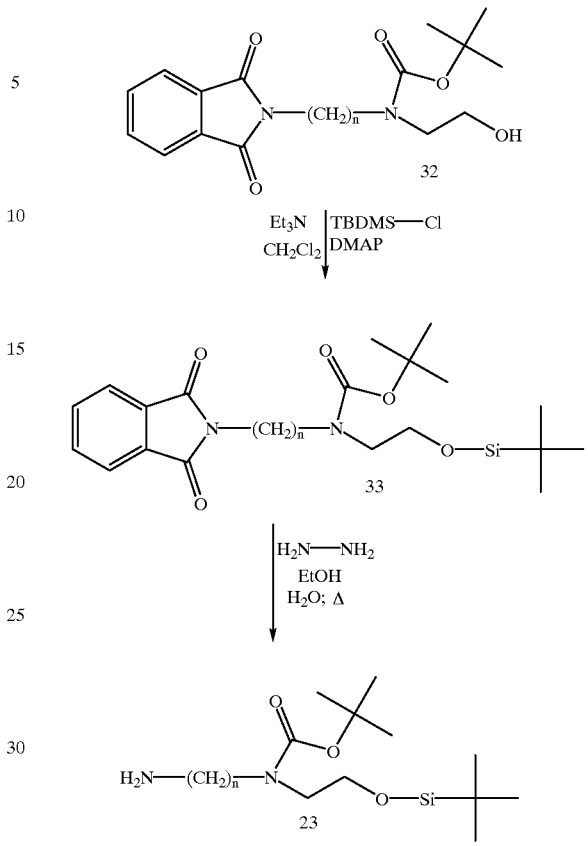

Diaminoalcohol 30 is allowed to react with phthalic anhydride in an inert solvent, such as dimethylformamide (DMF) at elevated temperature to give amine 31. Amine 31 is allowed to react with di-tert-butyl dicarbonate in an inert solvent, such as DMF to give amine 32. Reaction of 32 with a silylating agent, such as tert-butyldimethylsilyl chloride (TBDMS-Cl), in the presence of 4-dimethylaminopyridine (DMAP), and a base, such as triethylamine, in an inert solvent such as dichloromethane provides silylether 33. Removal of the phthalmide protecting group is effected by treating 33 with hydrazine hydrate in an alcoholic solvent, such as ethanol, at or below the reflux temperature to give amine 23.

The preparation of compounds of this invention encompassed by Formulae 8 and 10 is described hereinbelow in Flowsheet G wherein X is defined hereinabove, and Y is selected from n-butyl, sec-butyl, t-butyl, phenyl and Z is selected from n-butyl, sec-butyl, and t-butyl.

Aryl-bromide 34 wherein X is before defined, is allowed to undergo metal-halogen exchange with an aryl- or alkyl-lithium Y—Li wherein Y is before defined, in an inert solvent, such as ether at a temperature between −100° C. to room temperature. The resulting anion is allowed to react with trimethyl borate (B(OMe)$_3$), followed by an acidic work-up to provide 8.

In certain instances, it is possible to directly metallate aromatic substrates such as 35 wherein X is before defined, by reaction with alkyllithiums Z—Li wherein Z is before defined, in an inert solvent, such as ether, in the presence or absence of N,N,N',N'-tetramethylethylenediamine (TMEDA) at a temperature between −100° C. to room temperature. The resulting anion is allowed to react with B(OMe)$_3$, followed by an acidic work-up to provide 8.

The above anions can also be reacted with tributyltin chloride (nBu)$_3$SnCl to provide aryltin derivatives 10.

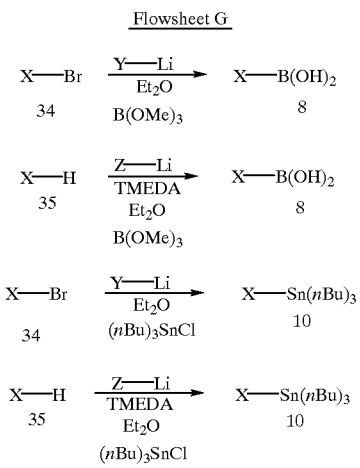

Flowsheet G

The preparation of compounds of this invention encompassed by Formula 43 is described hereinbelow in Flowsheet H wherein W, X, n, R$_1$, R$_2$, and R$_3$ are as defined hereinabove.

4-Bromophthalic anhydride 36 is reacted with sodium methoxide in a solvent such as methanol, at or about ambient temperature, to provide a mixture of two esters 37 and 38. The mixture of two esters may be separated by conventional means such as chromatography, recrystallization or distillation. Alternatively, the mixture of esters 37 and 38 are allowed to react with diphenylphosphoryl azide ((PhO)$_2$P(O)N$_3$) in an inert solvent, such as toluene, at a temperature between 23–150° C., followed by hydrolysis with aqueous acetone to provide a mixture of amines 39 and 40. The amines are readily separable from one another by chromatography, recrystallization or distillation.

Amine 39 is allowed to undergo condensation with 2-chloronicotinic acid (3) in a polar aprotic solvent such as ethanol, methanol, or aqueous ethanol, in the presence of a catalytic amount of a mineral acid such as hydrochloric acid at temperatures in excess of 80° C. to provide heterocycle 41. The carboxylic acid group within 41 can be converted into an amide 42 by reaction with amine 5 in the presence of a coupling agent, such as the BOP reagent, a base, such as Hünig's base, in an inert solvent such as dichloromethane. In some cases, mixtures of regioisomeric amides are formed from which the desired amide can be isolated by chromatography, distillation or recrystallization.

Compound 43 is prepared by a palladium (0) mediated coupling reaction of 42 with arylboronic acid 8, a catalytic amount of palladium (0), such as tetrakis(triphenylphosphine)palladium (0) (Pd(PPh$_3$)$_4$), a base such as sodium carbonate, in water, and an inert solvent such as toluene at or below reflux temperature.

An alternative approach to prepare amide 42 involves first transformation of acid 41 into its acid chloride 44 by reaction of 41 with oxalyl chloride, a catalytic amount of dimethylformamide, in an inert solvent such as dichloromethane. Acid chloride 44 is reacted with amine 5 in the presence of a base, such as triethylamine in an inert solvent, such as dichloromethane to give amide 42. In some cases, mixtures of regioisomeric amides are formed from which the desired amide can be isolated by chromatography, distillation, or recrystallization.

An alternative approach to compound 43 is reaction of bromide 42 with aryltin derivatives 10 in the presence of palladium (0), such as Pd(PPh$_3$)$_4$, in an inert solvent such as toluene, at or below the reflux temperature.

Flowsheet H

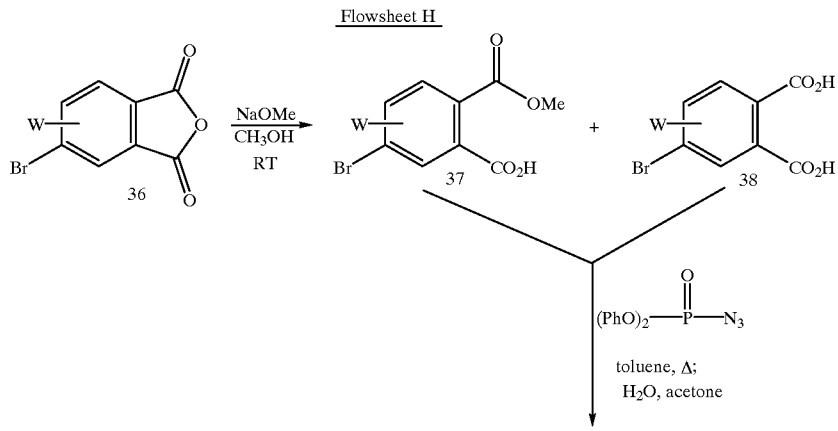

-continued
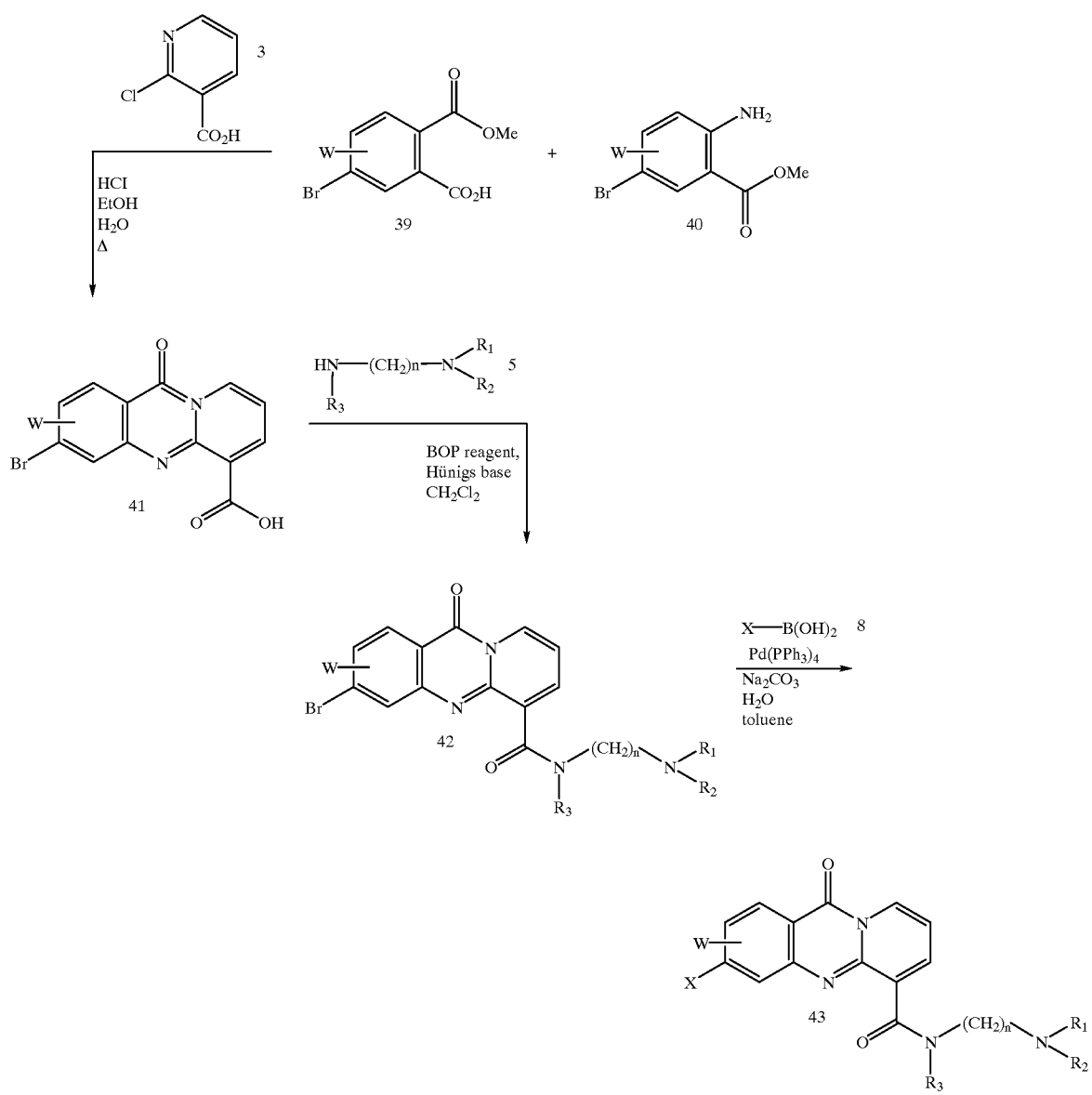
Flowsheet H (cont'd)
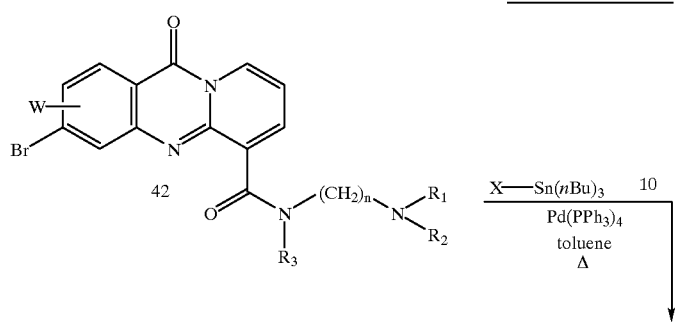

-continued

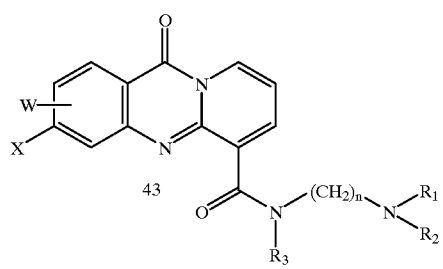

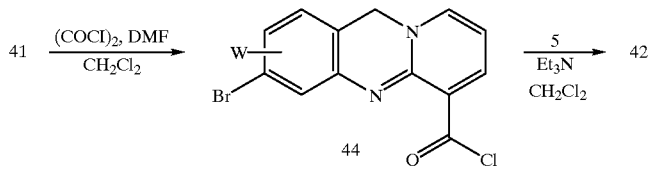

The pharmaceutically acceptable salts are those derived from pharmaceutically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The compounds of this invention are useful as antineoplastic agents as demonstrated by the results obtained for representative compounds of this invention in the following standard pharmacological test procedures.

Description of the two cell line test procedure

A2780 S and A2780 DDP cells [Biochemical and Molecular Properties of Cisplatin-resistant A2780 Cells Grown in Folinic Acid; Y. Lu, J. Hnan, and K. Scanlon, *J. Biol. Chem.*, 263, 4891–4894, 1988.] are grown in RPMI 1640 medium containing 5% fetal calf serum, 50 μg/ml streptomycin, 50 units/ml penicillin, 50 μg/ml gentamycin, 0.03% L-glutamine, 1 nM estradiol, 1 nM testosterone, 5 μg/mlinsulin, 5 μg/ml transferrin, and 5 ng/ml selenous acid, at 37° C., in a humidified atmosphere, containing 5% $CO_2$. Experiments are done in the same media.

Cells are plated at the concentration of $5 \times 10^4$/ml on Day 0 of the experiment. On Day one control cells are fixed with trichloroacetic acid and 5 ten fold dilutions of tested compounds are added, in duplicates, to the remaining cells. On Day 3 (48 hours exposure to drugs) all cells are fixed with trichloroacetic acid, stained with 0.4% sulforhodamine B, and absorbency is read at 520 nm. The $IC_{50s}$ (concentration causing 50% inhibition) are determined for each drug.

Murine Tumor Standard Pharmacological Test Procedures

Murine P388 Leukemia $CD2F_1$ mice are injected i.p. with $1 \times 10^6$ tumor cells on Day 0 of the test. Drugs are administered i.p. on Days 1, 5, and 9 after the tumor implantation. Positive drug response is indicated by a more than 25% increase in the mean life span (% ILS), relative to placebo treated controls. Drugs are considered to be toxic when the mean life span of the drug treated animals is more than 15% shorter than placebo treated controls.

Murine Colon 26 Advanced, Metastatic Tumor $CD2F_1$ mice are injected i.p. with $5 \times 10^5$ tumor cells on Day 0 of the test. Drugs are administered i.p. on Days 5, 9, and 13 after the tumor implantation. Positive drug response is indicated by a more than 25% increase in the mean life span (% ILS), relative to placebo treated controls. Drugs are considered to be toxic, when the mean life span of the drug treated animals is more than 15% shorter than placebo treated controls.

Human Tumor Xenograft Standard Pharmacological Test Procedure

Human tumor fragments are implanted s.c. in athyric nude mice. Tumors are allowed to grow until they attain a mass of 100–150 mgs. At Day 0 of the test, mice are placed into treatment groups such that mice in each group have approximately the same size tumors (tumor staging). Drugs are administered i.p. at Days 1, 5, and 9. Each mouse tumor mass is determined every 7 days, until Day 28, using caliper measurements of tumor length and width. Mean tumor mass for each group of animals is then calculated and the relative tumor growth determined. The relative tumor growth is defined as a ratio of the tumor mass on a given day to a tumor mass on Day 0. Calculation of % TIC (the relative tumor growth of treated group divided by the relative tumor growth of placebo group, multiplied by 100) is made for each day of measurement. A positive drug response is indicated by a % TIC value below 60%, and a p value in the Student t-test of less than 0.05. More than 20% deaths in the group related to the drug administration indicates toxicity.

TABLE 1

In Vitro Cytotoxicity Results in Two Cancer Cell Lines.
A2780 DDP and A2780 S Lines

| Example No. | $IC_{50}$ (μg/ml) A2780 S | $IC_{50}$ (μg/ml) A2780 DDP |
|---|---|---|
| 13 | 0.40 | 3.70 |
| 24 | 0.60 | 2.10 |
| 35 | 0.50 | 0.40 |
| 26 | 0.80 | 3.50 |
| 30 | 4.80 | 6.90 |
| 14 | 4.40 | 4.80 |
| 15 | 0.60 | 0.80 |
| 16 | 4.10 | 5.30 |
| 17 | 4.60 | 4.70 |
| 18 | 1.10 | 4.20 |
| 19 | 4.30 | 3.40 |
| 20 | 3.80 | 3.00 |
| 21 | 0.20 | 0.50 |

TABLE 2

In Vivo Murine Tumor Results

| Example No. | Dose (mg/kg) | Treatment schedule (d) | % ILS | Tumor Type |
|---|---|---|---|---|
| Placebo | — | 1,5,9 | — | P388 |
| Vincristine | 0.8 | 1,5,9 | +114 | P388 |
| 13 | 200 | 1,5,9 | +57 | P388 |
| 13 | 100 | 1,5,9 | +20 | P388 |
| 13 | 50 | 1,5,9 | +2 | P388 |
| 13 | 25 | 1,5,9 | +4 | P388 |
| 24 | 200 | 1,5,9 | 0 | P388 |
| 24 | 100 | 1,5,9 | +4 | P388 |
| 24 | 50 | 1,5,9 | +4 | P388 |
| 24 | 25 | 1,5,9 | +12 | P388 |
| 15 | 200 | 1,5 | −40 | P388 |
| 15 | 100 | 1,5,9 | +2 | P388 |
| 15 | 50 | 1,5,9 | +8 | P388 |
| 19 | 200 | 1,5,9 | +6 | P388 |
| 19 | 100 | 1,5,9 | +4 | P388 |
| 19 | 50 | 1,5,9 | −9 | P388 |
| Placebo | — | 5,9,13 | — | COLON 26 |
| Adriamycin | 4 | 5,9,14 | +71 | COLON 26 |
| 13 | 250 | 5,9,13 | +35 | COLON 26 |
| 13 | 200 | 5,9,13 | +24 | COLON 26 |
| 13 | 100 | 5,9,13 | +18 | COLON 26 |
| 24 | 300 | 5,9,13 | −24 | COLON 26 |
| 24 | 200 | 5,9,13 | +24 | COLON 26 |
| Vincristine | 1.0 | 1,5,9 | 52% T/C | LS174T |
| 13 | 300 | 1,5,9 | 44% T/C | LS174T |
| 13 | 250 | 1,5,9 | 59% T/C | LS174T |

Based on the results obtained in the standard pharmacological test procedures described above, the compounds of this invention are useful as antineoplastic agents. More particularly, the compounds of this invention are useful for inhibiting the growth of neoplastic cells, causing cell death of neoplastic cells, and eradicating neoplastic cells. The compounds of this invention are therefore useful for treating solid tumors, including sarcomas and carcinomas, such as astrocytomas, prostate cancer, breast cancer, small cell lung cancer, and ovarian cancer; leukemias; lymphomas; adult T-cell leukemia/lymphoma; and other neoplastic disease states.

In addition to the utilities described above, many of the compounds of this invention are useful in the preparation of other compounds of this invention.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups and the like. Such compositions and preparations should contain at least 0.1% of active compound. The percentage of the compound in these compositions may, of course, be varied and may conveniently be between about 2% to about 60% of the weight of the unit The amount of active compound in such therapeutically useful compositions is such that a suitable dosage will be obtained. Preferred compositions according to this invention are prepared so that an oral dosage unit contains between about 1 and 250 mg of active compound.

The tablets, capsules and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to active ingredient, sucrose as a sweetening agent, methyl and propylparabens as preservatives, a dye and flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention may also be administered directly to the airways in the form of an aerosol.

The following examples describe the perparation of representative compounds of this invention.

EXAMPLE 1

Carbamic acid, [[(2-aminoethyl)iminol-di-2,1-ethanediyl]bis,bis(1,1-dimethyl-ethyl)ester To a 0° C. solution of tris(2-aminoethyl)amine (10.0 g; 68.4 mmol), triethylamine (28.6 ml; 205 mmol) and dry tetrahydrofuran (THF; 100 ml) was added a solution of 2-(tert-butoxycarbonyloxyimino)-2-phenylacetonitile (BOC—ON Reagent; 33.7 g; 136.8 mmol) dissolved in dry THF (200 ml) dropwise. The reaction mixture was stirred at 0° C. for 4 hours, diluted with dichloromethane (150 ml) and washed with brine (100 ml). The organic phase was separated, dried over anhydrous sodium sulfate, filtered and concentrated in vacuo. The residue was purified by flash chromatography on silica gel (250 g; elution with 10% methanol/chloroform) to provide product as a pale yellow oil: 11.06 g.

$^1$H NMR (300 MHz, CDCl$_3$) δ5.28(br s, 2H), 3.20(m, 4H), 2.70(m, 2H), 2.52(m, 4H), 1.75(br, 2H), 1.47(s, 18H).

EXAMPLE 2

Carbamic acid, (2-aminoethyl)-1,1-dimethylethyl ester

To a 0° C. solution of ethylenediamine (137.7 g; 2.29 mol) dissolved in dry tetrahydrofuran (1 L) was added di-tert-butyl dicarbonate (100 g; 458 mmol) dissolved in dry tetrahydrofuran (250 ml) dropwise with mechanical stirring. The dropping funnel was rinsed with tetrahydrofuran (167 ml). The reaction mixture was allowed to warm to room temperature and maintained at that temperature for 1 hour, prior to dilution with brine (1 L). The aqueous phase was extracted with chloroform (3×750 ml). The combined organic phases were dried over anhydrous sodium sulfate, filtered, and concentrated in vacuo. The residue was purified by flash chromatography on silica gel (650 g; elution with 5–20% methanol/chloroform) to provide product as a pale yellow oil: 49.94 g.

$^1$H NMR (300 MHz, CDCl$_3$) δ4.94(br s, 1H), 3.19(m, 2H), 2.79(m, 2H), 1.49(s, 9H).

EXAMPLE 3

Carbamic acid, (iminodi-2,1-ethanediyl)bis-,bis(1,1-dimethylethyl) ester

To a 0° C. solution of diethylenetriamine (5 g; 48.5 mmol) dissolved in dry tetrahydrofuran (150 ml) and triethylamine (20.3 ml; 145 mmol) was added a solution of 2-(tert-butoxycarbonyloxyimino)-2-phenylacetonitrile (BOC—ON Reagent; 23.87 g; 96.9 mmol) dissolved in dry tetrahydrofuran (288 ml) dropwise over 1 hour. The reaction mixture was maintained at 0° C. for 3 hours, prior to concentration in vacuo. The residue was suspended in 1 N sodium hydroxide (150 ml) and brine (150 ml) and extracted with chloroform (4×250 ml). The organic layers were combined, dried over anhydrous sodium sulfate, filtered, and concentrated in vacuo. The residue was purified by flash chromatography on silica gel (150 g; elution with 10% methanol/chloroform) to provide product as a colorless oil: 12.62 g.

$^1$H NMR (300 MHz, CDCl$_3$) δ4.95(br s, 2H), 3.21(q, 4H), 2.71(t, 4H), 1.50(s, 18H).

EXAMPLE 4

Carbamic acid, [2-(1,3-dihydro-1,3-dioxo-2H-isoindol-2-yl)ethyl](2-hydroxy-ethyl)-,1,1-dimethylethyl ester A solution of 2-(2-aminoethylamino)ethanol (20 g; 192.0 mmol) and phthalic anhydride (31.3 g; 211.2 mmol) and dry dimethylformamide (52 ml) was heated at 145° C. for 18 hours, then cooled to room temperature. The dimethylformamide was removed in vacuo. The residue was dissolved in dimethylformamide (100 ml) and cooled to 0° C. To this solution was added a solution of di-tert-butyl dicarbonate (41.91 g; 192 mmol) dissolved in dimethylformamide (100 ml) dropwise over 30 minutes. The solution was warmed to room temperature and maintained at ambient temperature for 6 hours prior to concentration in vacuo. The residue was suspended in brine (350 ml), and extracted with chloroform (3×400 ml). The combined organic phases were dried over anhydrous sodium sulfate, filtered and concentrated in vacuo. The residue was purified three times by flash chromatography on silica gel (200 g; elution with 70% ethyl acetate/hexane) to provide product as a colorless solid: 9.14 g.

$^1$H NMR (300 MHz CDCl$_3$) δ7.85–7.70(m, 4H), 3.94–3.30(m, 8H), 1.20(s, 9H). Anal: calcd for C$_{17}$H$_{22}$N$_2$O$_5$: C, 61.07; H, 6.63; N, 8.38. Found: C, 61.07; H, 6.70; N, 8.01.

EXAMPLE 5

Carbamic acid, [2-(1,3-dihydro-1,3-dioxo-2H-isoindol-2-yl)ethyl][2-[[(1,1-dimethylethyl)-dimethylsilyl]oxy]ethyl]-,1,1-dimethylethyl ester To a 0° C. solution of carbamic acid, [2-(1,3-dihydro-1,3-dioxo-2H-isoindol-2-yl)ethyl](2-hydroxyethyl)-,1,1-dimethylethyl ester (10.82 g; 32.4 mmol) dissolved in dry dichloromethane (60 ml), triethylamine (22.6 ml; 161.8 mmol), and 4-dimethylaminopyridine (197.7 mg; 1.62 mmol) was added tert-butyldimethylsilyl chloride (4.88 g; 32.4 mmol). The solution was allowed to warm to room temperature overnight, prior to dilution with brine (250 ml). The aqueous layer was extracted with dichloromethane (4×250 ml). The combined organic phases were dried over anhydrous sodium sulfate, filtered and concentrated in vacuo. The residue was purified by flash chromatography on silica gel (555 g; elution with 2% methanol/chloroform) to provide product as a pale yellow oil: 14.52 g.

$^1$H NMR (300 MHz, CDCl$_3$) δ7.89–7.65(m, 4H), 3.80–3.25(m, 8H), 1.20(s, 9H), 0.87(s, 9H), 0.0(s, 6H).

EXAMPLE 6

Carbamic acid, (2-aminoethyl)[2-[[(1,1-dimethylethyl)-dimethylsilyl]oxy]ethyl]-,1,1-dimethylethyl ester A solution of carbamic acid, [2-(1,3-dihydro-1,3-dioxo-2H-isoindol-2-yl)ethyl][2-[[(1,1-dimethylethyl)dimethylsilyl]oxy]ethyl]-,1,1-dimethylethyl ester (14.52 g; 32.4 mmol), hydrazine hydrate (7.85 ml; 161.8 mmol) and ethanol (500 ml) was heated at reflux for 18 hours with mechanical stirring. The reaction mixture was cooled to room temperature and filtered. The filtrate was concentrated to dryness, then re-suspended in ether (500 ml), and filtered again. The filtrate was concentrated to dryness then re-suspended in ether (500 ml) and filtered. The filtrate was concentrated to dryness to provide a pale yellow oil: 8.53 g.

FAB MS: m/z 319 (M$^+$+H). $^1$H NMR (300 MHz, CDCl$_3$) δ3.70–3.65(m, 2H), 3.25–3.35(m, 4H), 2.76(t, 2H), 1.45(s, 9H), 0.80(s, 9H), 0.05(s, 6H).

EXAMPLE 7

Boronic acid, [1,1'-biphenyl]-2-yl-

To a −78° C. solution of tert-butyllithium (25.2 ml of a 1.7 molar solution in pentane; 42.9 mmol) in ether (125 ml) was added 2-bromobiphenyl (5.0 g; 21.5 mmol) in one portion. Fifteen minutes later ether (20 ml) was added. After fifteen minutes more, trimethyl borate (12.2 ml; 107.3 mmol) was added; stirring was continued at −78° C. for 30 minutes, followed by warming to room temperature. The reaction mixture was diluted with water (200 ml) and stirred at room temperature for 30 minutes. The aqueous layer was extracted with ether (3×100 ml). The combined ether layers were washed with brine (100 ml), dried over anhydrous magnesium sulfate, filtered and concentrated in vacuo. The residue (4.0 g) was a thick colorless oil which congealed upon standing and was used directly in subsequent experiments.

EXAMPLE 8

Boronic acid, [1,1'-biphenyl]-3-yl-

To a −78° C. solution of 3-bromobiphenyl (5.0 g; 21.5 mmol) dissolved in ether (125 ml) was added tert-butyllithium (25.2 ml of a 1.7 molar solution in pentane; 42.9 mmol) during 5 minutes. Stirring at −78° C. was continued for 1 hour. To the cold solution was added trimethyl borate (12.2 ml; 107.3 mmol) during 2 minutes; stirring was continued at −78° C. for 1 hour, then warmed to room temperature during 1 hour. To this solution was added water (200 ml) and 10% aqueous hydrochloric acid (30 ml) and stirring was continued for 10 minutes, prior to extraction with ether (3×100 ml). The combined organic phases were washed with brine (100 ml), dried over anhydrous magnesium sulfate, filtered and concentrated in vacuo. The ivory solid isolated (4.0 g) was used directly in subsequent experiments.

EXAMPLE 9

Boronic acid, [3-(dimethylamino)phenyl]-

To a −78° C. solution of n-butyllithium (4.8 ml of a 2.5 molar solution in hexanes; 12 mmol) in ether (5 ml) was added 3-bromo-N,N-dimethylaniline (1.72 g, 10.0 mmol, Giumanini, A. G., Chiavari, G., Musiani, M. M., Rossi, P., Synthesis, 1980, 743.) dropwise. Five minutes later, a solution of trimethylborate (1.35 ml 13 mmol) in 5 ml. of ether was added dropwise over 10 minutes. The reaction was stirred for 1 hour then warmed to room temperature and stirred overnight. The reaction mixture was diluted with water (20 ml), and concentrated in vacuo. To the residue was added glacial acetic acid (HOAc) (1.5 ml) and EtOH (20 ml). The resulting mixture was then heated at reflux for 30 minutes, and concentrated in vacuo. The residue (3.16 g) was a clear yellow oil which solidified to a thick white gum.

EXAMPLE 10

11H-Pyrido[2,1-b]quinazoline-6-carboxylic acid, 2-iodo-11-oxo

A solution of 2-amino-5-iodobenzoic acid (25 g; 95.0 mmol), 2-chloronicotinic acid (14.97 g; 95.0 mmol), concentrated hydrochloric acid (3.17 ml; 38 mmol), and ethanol (150 ml) was heated at reflux for 18 hours, then cooled to 0° C. The precipitate was collected by filtration and the filter cake was washed with fresh ethanol (200 ml). The filter cake was dried in vacuo over phosphorous pentoxide to provide product as a yellow solid: 12.0 g.

FAB MS: m/z 367 (M$^+$+H). $^1$H NMR (300 MHz, DMSO.d$_6$) δ9.15(d, 1H), 8.65(d, 1H), 8.57(s, 1H), 8.26(d, 1H), 7.75(d, 1H), 7.28(t, 1H).

EXAMPLE 11

11H-Pyrido[2,1-b]quinazoline-6-carboxamide, N-[2-(dimethylamino)ethyl]-2-iodo-11-oxo- To a room temperature solution of 11H-pyrido[2,1-b]quinazoline-6-carboxylic acid, 2-iodo-11-oxo (25 g; 62.1 mmol), N,N-dimethylethylenediamine (7.16 ml; 65.2 mmol), N,N-diisopropylethylamine (108.2 ml; 621 mmol), and dichloromethane (570 ml) was added benzotriazol-1-yloxytris(dimethylamino)phosphonium hexafluorophosphate (35.71 g; 80.7 mmol) in one portion. After a stirring period of 18 hours, the reaction mixture was diluted with 1 N sodium hydroxide (700 ml), and extracted with dichloromethane (3×500 ml). The combined organic phases were washed with brine (700 ml), dried over anhydrous sodium sulfate, filtered and concentrated in vacuo. The residue was recrystallized repeatedly from hot methanol to provide product as a yellow solid: 19.21 g.

FAB MS: m/z 375 (M$^+$+H). $^1$H NMR (300 MHz, CDCl$_3$) δ11.45(m, 1H), 9.05(d, 1H), 8.87(d, 1H), 8.75(s, 1H), 8.09 (d, 1H), 7.52(d, 1H), 7.05(t, 1H), 3.65(q, 2H), 2.60(t, 2H), 2.41(s, 6H).

EXAMPLE 12

11H-Pyrido[2,1-b]quinazoline-6-carboxamide, 2-iodo-11-oxo-N-[2-(1-pyrrolidinyl) ethyl]

To a room temperature solution of 11H-pyrido[2,1-b]quinazoline-6-carboxylic acid, 2-iodo-11-oxo (2.0 g; 4.97 mmol), 1-(2-aminoethyl)pyrrolidine (1.26 ml; 9.94 mmol), N,N-diisopropylethylamine (4.33 ml; 24.8 mmol), and dichloromethane (50 ml) was added benzotriazol-1-yloxytris(dimethylamino)phosphonium hexafluorophosphate (3.3 g; 7.45 mmol) in one portion. After a stirring period of 66 hours, the reaction mixture was diluted with half-saturated sodium bicarbonate (100 ml) and extracted with dichloromethane (3×50 ml). The combined organic phases were washed with brine (70 ml), dried over anhydrous magnesium sulfate, filtered and concentrated in vacuo. The residue was purified by repeated flash chromatography. The first purification (250 g silica gel; elution with 10% methanol/chloroform) was followed by a second purification (250 g; elution with 45% methanol/ethyl acetate followed by a gradient elution 10–20% methanol/chloroform) to provide product as a bright lemon yellow solid: 1.82 g.

$^1$H NMR (300 MHz, CDCl$_3$) δ11.45(m, 1H), 9.02(dd, 1H), 8.84(dd, 1H), 8.78(d, 1H), 8.09(dd, 1H), 7.54(d, 1H), 7.05(t, 1H), 3.70(q, 2H), 2.81(t, 2H), 2.56(m, 4H), 1.89(m, 4H).

EXAMPLE 13

11H-Pyrido[2,1-b]quinazoline-6-carboxamide, 2-(3-aminophenyl)-N-[2-(dimethylamino)ethyl]-11-oxo A degassed solution of 11H-pyrido[2,1-b]quinazoline-6-carboxamide, N-[2-(dimethylamino)ethyl]-2-iodo-11-oxo- (2.95 g; 6.76 mmol), 3-aminophenylboronic acid monohydrate (2.41 g; 15.6 mmol), tetrakis(triphenylphosphine) palladium (0) (781.4 mg; 0.68 mmol), 2 M sodium carbonate solution (16.9 ml; 33.8 mmol) and toluene (130 ml) was heated at reflux for 7 hours. An additional quantity of tetrakis(triphenylphosphine)palladium (0) (0.411 g; 0.36 mmol) was added and reflux was continued for 5 hours more. The reaction mixture was cooled to room temperature, diluted with water (200 ml), and extracted with chloroform (3×250 ml). The combined organic phases were dried with anhydrous sodium sulfate, filtered, and concentrated in vacuo. The residue was purified by flash chromatography on silica gel (150 g; elution with 15% methanol/chloroform) to provide product as a yellow solid: 1.07 g.

FAB MS: m/z 402 (M$^+$+H). $^1$H NMR (300 MHz, CDCl$_3$) δ11.51(br s, 1H), 9.05(m, 1H), 8.80(m, 1H), 8.21(d, 1H), 8.15(m, 1H), 7.81(d, 1H), 7.25(m, 1H), 7.15–7.0(m, 3H), 6.75(m, 1H), 3.78(m, 2H), 3.70(q, 2H), 2.65(t, 2H), 2.45(s, 6H).

EXAMPLE 14

11H-Pyrido[2,1-b]quinazoline-6-carboxamide, 2-[1,1'biphenyl]-2-yl-N-[2-(dimethylamino)ethyl]-11-oxo A degassed solution of 11H-pyrido[2,1-b]quinazoline-6-carboxamide, N-[2-(dimethylamino)ethyl]-2-iodo-11-oxo- (0.50 g; 1.15 mmol), boronic acid,[1,1'-biphenyl]-2-yl (1.59 g; 8.02 mmol), tetrakis(triphenylphosphine)palladium (0) (0.331 g; 0.29 mmol), 2 M sodium carbonate solution (2.87 ml; 5.73 mmol), and toluene (30 ml) was heated at reflux for 6 hours, and then cooled to room temperature. The reaction mixture was diluted with water (100 ml) and extracted with dichloromethane (3×150 ml). The combined organic phases were washed with brine (100 ml), dried over anhydrous magnesium sulfate, filtered, and concentrated in vacuo. The residue was purified by flash chromatography on silica gel (60 g; gradient elution 0–10% methanol/chloroform) to provide product as an orange-yellow solid: 0.40 g.

FAB MS: m/z 463 (M$^+$+H). $^1$H NMR (300 MHz, CDCl$_3$) δ11.45(m, 1H), 9.05(dd, 1H), 8.78(dd, 1H), 8.49(d, 1H), 7.57–7.43(m, 6H), 7.23–7.12(m, 5H), 7.00(t, 1H), 3.64(q, 2H), 2.60(t, 2H), 2.33(s, 6H).

EXAMPLE 15

11H-Pyrido[2,1-b]quinazoline-6-carboxamide, 2-[1,1'-biphenyl]-3-yl-N-[2-(dimethylamino)ethyl]-11-oxo A degassed solution of 11H-pyrido[2,1-b]quinazoline-6-carboxamide, N-[2-(dimethylamino)ethyl]-2-iodo-11-oxo- (0.50 g; 1.15 mmol), boronic acid, [1,1'-biphenyl]-3-yl-(1.59 g; 8.02 mmol), tetrakis(triphenylphosphine)palladium (0) (0.331 g; 0.29 mmol), 2 M sodium carbonate solution (2.87 ml; 5.73 mmol), and toluene (30 ml) was heated at reflux for 35 minutes, then cooled to room temperature. The reaction mixture was diluted with water (100 ml) and extracted with dichloromethane (3×150 ml). The combined organic phases were washed with brine (100 ml), dried with anhydrous magnesium sulfate, filtered and concentrated in vacuo. The residue was purified by flash chromatography on silica gel (50 g; gradient elution 0–5% methanol/chloroform) to provide product as a yellow solid: 0.431 g.

FAB MS: m/z 463 (M$^+$+H). $^1$H NMR (300 MHz, CDCl$_3$) δ11.51(br s, 1H), 9.08(dd, 1H), 8.82(dd, 1H), 8.71(d, 1H), 8.21(dd, 1H), 7.94–7.87(m, 2H), 7.74–7.39(m, 8H), 7.04(t, 1H), 3.70(q, 2H), 2.67(t, 2H), 2.42(s, 6H).

EXAMPLE 16

11H-Pyrido[2,1-b]quinazoline-6-carboxamide, N-[2-(dimethylamino)ethyl-11-oxo-2-(9-phenanthrenyl)

A degassed solution of 11H-pyrido[2,1-b]quinazoline-6-carboxamide, N-[2-(dimethylamino)ethyl]-2-iodo-11-oxo- (0.49 g; 1.12 mmol), 9-phenanthreneboronic acid (299 mg; 1.35 mmol), tetrakis(triphenylphosphine)palladium (0) (129 mg; 0.11 mmol), 2 M sodium carbonate solution (2.81 ml; 5.62 mmol), and toluene (22 ml) was heated at reflux for 4 hours, cooled to room temperature, diluted with water (70 ml), and extracted with chloroform (3×100 ml). The combined organic phases were dried with anhydrous sodium sulfate, filtered, and concentrated in vacuo. The residue was purified by flash chromatography repeatedly (55 g silica gel; elution with 5–10% methanol/chloroform; and 2–20% methanol/ethyl acetate) to provide product as a yellow solid: 436 mg.

FAB MS: m/z 487 (M$^+$+H). $^1$H NMR (300 MHz, CDCl$_3$) δ11.58(br s, 1H), 9.09(dd, 1H), 8.88–8.74(m, 3H), 8.67(d, 1H), 8.10(dd, 1H), 7.96–7.48(m, 3H), 7.80(s, 1H), 7.74–7.54(m, 4H), 7.05(t, 1H), 3.75(q, 2H), 2.65(t, 2H), 2.47(s, 6H).

EXAMPLE 17

11H-pyrido[2,1-b]quinazoline-6-carboxamide, N-[2-(dimethylamino)ethyl]-2-(1-naphthalenyl)-11-oxo A degassed solution of 11H-pyrido[2,1-b]quinazoline-6-carboxamide, N-[2-(dimethylamino)ethyl]-2-iodo-11-oxo- (0.49 g; 1.12 mmol), 1-naphthaleneboronic acid (386 mg; 2.25 mmol), tetrakis(triphenylphosphine)palladium (0) (129.8 mg; 0.11 mmol) 2 M sodium carbonate solution (2.81 ml; 5.62 mmol), and toluene (22 ml) was heated at reflux for 8 hours, cooled to room temperature, diluted with water (70 ml) and extracted with chloroform (3×100 ml). The combined organic phases were dried with anhydrous sodium sulfate, filtered, and concentrated in vacuo. The residue was purified by flash chromatography several times (55 g silica gel; elution with 10% methanouchloroform; and 2–30% methanol/ethyl acetate) to provide product as a yellow solid: 485 mg.

FAB MS: m/z 437 (M$^+$+H). $^1$H NMR (300 MHz, CDCl$_3$) δ11.57(br s, 1H), 9.08(m, 1H), 8.78(m, 1H), 8.60(s, 1H), 8.07–7.80(m, 5H), 7.60–7.45(m, 4H), 7.08(t, 1H), 3.74(q, 2H), 2.70(t, 2H), 2.45(s, 6H).

EXAMPLE 18

11H-Pyrido[2,1-b]quinazoline-6-carboxamide, N-[2-(dimethylamino)ethyl]-11-oxo-2-[3-(trifluoromethyl)phenyl A degassed solution of 11H-pyrido[2,1-b]quinazoline-6-carboxamide, N-[2-(dimethylamino)ethyl]-2-iodo-11-oxo- (0.5 g; 1.15 mmol), (trifluoromethyl)benzeneboronic acid (435 mg; 2.29 mmol), tetrakis(triphenylphosphine) palladium (0) (132 mg; 0.11 mmol), 2 M sodium carbonate solution (2.87 ml; 5.73 mmol), and toluene (23 ml) was heated at reflux for 12 hours, cooled to room temperature, diluted with water (70 ml) and extracted with chloroform (3×100 ml). The combined organic phases were dried with anhydrous sodium sulfate, filtered and concentrated in vacuo. The residue was purified by flash chromatography several times (55 g silica gel; elution with 10% methanol/chloroform; and 2–20% methanol/ethyl acetate) to provide product as a yellow solid: 389 mg.

FAB MS: m/z 455 (M$^+$+H). $^1$H NMR (300 MHz, CDCl$_3$) δ11.49(br s, 1H), 9.09(dd, 1H), 8.84(dd, 1H), 8.69(d, 1H), 8.16(dd, 1H), 8.0–7.88(m, 3H), 7.71–7.61(m, 2H), 7.07(t, 1H), 3.71(q, 2H), 2.62(t, 2H), 2.43(s, 6H).

EXAMPLE 19

11H-Pyrido[2,1-b]quinazoline-6-carboxamide, N-[2-(dimethylamino)ethyl]-2-(4-methoxyphenyl)-11-oxo A degassed solution of 11H-pyrido[2,1-b]quinazoline-6-carboxamide, N-[2-(dimethylamino)ethyl]-2-iodo-11-oxo- (0.5 g; 1.15 mmol), 4-methoxybenzeneboronic acid (348 mg; 2.29 mmol), tetrakis(triphenylphosphine)palladium (0) (132 mg; 0.11 mmol), 2 M sodium carbonate solution (2.87 ml; 5.73 mmol), and toluene (23 ml) was heated at reflux for 12 hours, cooled to room temperature, diluted with water (70 ml), and extracted with chloroform (3×100 ml). The combined organic phases were dried with anhydrous sodium sulfate, filtered and concentrated in vacuo. The residue was purified by flash chromatography several times (55 g silica gel; elution with 10% methanol/chloroform; and 2–20% methanol/ethyl acetate) to provide product as a yellow solid: 438 mg.

FAB MS: m/z 417 (M$^+$+H). $^1$H NMR (300 MHz, CDCl$_3$) δ11.52(br s, 1H), 9.05(dd, 1H), 8.80(dd, 1H), 8.62(d, 1H), 8.13(dd, 1H), 7.83(d, 1H), 7.72–7.66(m, 2H), 7.08–6.99(m, 3H), 3.88(s, 3H), 3.69(q, 2H), 2.66(t, 2H), 2.43(s, 6H).

EXAMPLE 20

11H-Pyrido[2,1-b]quinazoline-6-carboxamide, 2-[3,5-bis(trifluoromethyl)phenyl]-N-[2-(dimethylamino)ethyl]-11-oxo A degassed solution of 11H-pyrido[2,1-b]quinazoline-6-carboxamide, N-[2-(dimethylamino)ethyl]-2-iodo-11-oxo- (250 mg; 0.57 mmol), 3,5-bis(trifluoromethyl) benzeneboronic acid (177 mg; 0.69 mmol), tetrakis (triphenylphosphine)palladium (0) (166 mg; 0.14 mmol), 2 M sodium carbonate solution (1.43 ml; 2.87 mmol) and toluene (15 ml) was heated at reflux for 2 hours, cooled to room temperature, diluted with water (100 ml) and extracted with chloroform (3×150 ml). The combined organic phases were dried with anhydrous sodium sulfate, filtered and concentrated in vacuo. The residue was purified by flash chromatography (55 g silica gel; elution with 10% methanol/chloroform) to give product as a yellow solid: 263 mg.

$^1$H NMR (300 MHz, CDCl$_3$) δ11.49(br s, 1H), 9.05(dd, 1H), 8.81(dd, 1H), 8.72(d, 1H), 8.18–7.79(m, 5H), 7.09(t, 1H), 3.77(q, 2H), 2.83(t, 2H), 2.55(s, 6H).

EXAMPLE 21

11H-Pyrido[2,1-b]quinazoline-6-carboxamide, N-[2-(dimethylamino)ethyl]-2-[3-(dimethylamino)phenyl-11-oxo A mixture of crude boronic acid, [3-(dimethylamino)phenyl] (3.16 g), 11H-pyrido[2,1-b]quinazoline-6-carboxamide, N-[2-(dimethylamino)ethyl]-2-iodo-11-oxo-(100 mg, 0.23 mmol), tetrakis(triphenylphosphine)palladium (0) (68.2 mg, 0.059 mmol), 2M sodium carbonate solution (0.57 ml, 1.14 mmol) was heated to 120–125° C. in an oil bath for 45 min, and then cooled to room temperature. The dark brown residue was partitioned between ethyl acetate (EtOAc) and potassium carbonate (K$_2$CO$_3$), dried with sodium sulfate, and concentrated in vacuo. The residue was purified by flash chromatography on silica gel (5% methanol in chloroform) to provide product as a yellow brown solid: 17.3 mg.

CI MS: m/z 430 (M$^+$+H). $^1$H NMR (300 MHz, CDCl$_3$) δ11.55 (s, 1H), 9.05 (m, 1H), 8.79 (m, 1H), 8.66 (m, 1H), 8.15 (m, 1H), 7.86 (m, 1H), 7.52 (m, 1H), 7.37 (m, 1H), 7.03 (m, 3H), 6.80 (m, 1H), 3.71 (m, 2H), 3.05 (s, 6H), 2.66 (t, 2H), 2.43 (s, 6 H).

EXAMPLE 22

Carbamic acid, [2-[[(1,1-dimethylethyl)dimethylsilyl]oxy]ethyl][2-[[(2-iodo-11-oxo-11H-pyrido[2,1-b]guinazolin-6-yl)carbonyl]amino]ethyl], 1,1-dimethylethyl ester To a room temperature solution of 11H-pyrido [2,1-b]quinazoline-6-carboxylic acid, 2-iodo-11-oxo (2.0 g; 4.97 mmol), carbamic acid, (2-aminoethyl) [2-[[(1,1-dimethylethyl)dimethylsilyl]oxy]ethyl]-, 1,1-dimethylethyl ester (1.74 g; 5.46 mmol), N,N-diisopropylethylamine (8.65 ml; 49.7 mmol) and anhydrous dichloromethane (49 ml) was added the BOP reagent (2.86 g; 6.46 mmol) in one portion. The reaction mixture was stirred for 18 hours, diluted with brine (100 ml) and extracted with chloroform (3×100 ml). The combined organic phases were dried with anhydrous sodium sulfate, filtered and concentrated in vacuo. The residue was purified by flash chromatography (150 g silica gel; elution with 30% ethyl acetate/hexane) followed by recrystallization from chloroform to provide product as a yellow solid: 1.29 g.

$^1$H NMR (300 MHz, CDCl$_3$) δ11.01(br s, 1H), 9.05(m, 1H), 8.82(m, 1H), 8.78(d, 1H), 8.11(m, 1H), 7.62(m, 1H), 7.02(t, 1H), 3.82–3.30(m, 8H), 1.46(s, 9H), 0.87(s, 9H), 0.0(s, 6H).

EXAMPLE 23

Carbamic acid, [2-[[[2-(3-aminophenyl)-11-oxo-11H-pyrido[2,1-b]quinazolin-6-yl]carbonyl]amino]ethyl][2-[[(1,1-dimethylethyl)dimethylsilyl]oxy]ethyl], 1,1-dimethylethyl ester A degassed solution of carbamic acid, 2-[[(1,1-dimethylethyl)dimethylsilyl]oxy]ethyl][2-[[(2-iodo-11-oxo-11H-pyrido[2,1-b]quinazolin-6-yl)carbonyl]amino]ethyl], 1,1-dimethylethyl ester (1.29 g; 1.94 mmol), 3-aminophenylboronic acid hydrate (690 mg; 4.45 mmol); tetrakis(triphenylphosphine)palladium (0) (224 mg; 0.19 mmol), 2 M sodium carbonate solution (4.84 ml; 9.68 mmol), and toluene (52 ml) was heated at reflux for 5 hours, cooled to room temperature, diluted with water (100 ml) and extracted with dichloromethane (3×200 ml). The combined organic phases were dried with anhydrous sodium sulfate, filtered, and concentrated in vacuo. The residue was purified by flash chromatography (150 g silica gel; elution with 40% ethyl acetate/hexane) to provide product as a yellow foam: 0.903 g.

$^1$H NMR (300 MHz, CDCl$_3$) δ11.25(br, 1H), 9.05(m, 1H), 8.74(m, 1H), 8.09(s, 1H), 8.10–7.75(m, 2H), 7.24(m, 1H), 7.09–6.99(m, 3H), 6.72(m, 1H), 3.80–3.35(m, 8H), 1.41(s, 9H), 0.79(s, 9H), 0.0(s, 6H).

EXAMPLE 24

11H-Pyrido [2,1-b]quinazoline-6-carboxamide, 2-(3-aminophenyl)-N-[2-[(2-hydroxyethyl)amino]ethyl]-11-oxo-trihydrochloride A solution of carbamic acid, [2-[[[2-(3-aminophenyl)-11-oxo-11H-pyrido[2,1-b]quinazolin-6-yl]carbonyl]amino]ethyl][2-[[(1,1-dimethylethyl)dimethylsilyl]oxy]ethyl], 1,1-dimethylethyl ester (0.903 g; 1.43 mmol), 6 N hydrochloric acid (29 ml), and methanol (55 ml) was stirred at room temperature for 18 hours. The reaction mixture was concentrated to dryness then redissolved in ethanol (100 ml). This procedure was re. The residue was washed with ether to provide product as a pale yellow solid: 0.614 g.

FAB MS: m/z 531 (M$^+$+H). $^1$H NMR (300 MHz, DMSO-d$_6$) δ11.02(t, 1H), 9.09(dd, 1H), 8.99(m, 1H), 8.63(dd, 1H), 8.57(s, 1H), 8.30(dd, 1H), 8.24(d, 1H), 7.81(m, 1H), 7.65(t, 1H), 7.42(m, 1H), 7.30(t, 1H), 3.81(q, 2H), 3.72(t, 2H), 3.26(m, 2H), 3.16(m, 2H).

EXAMPLE 25

Carbamic acid, [2-[[(1,1-dimethylethyl)dimethylsilyl]oxy]ethyl][2-[[(11-oxo-2-phenyl-11H-pyrido[2,1-b]quinazolin-6-yl)carbonyl]amino]ethyl], 1,1-dimethylethyl ester A degassed solution of carbamic acid, [2[[(1,1-dimethylethyl)dimethylsilyl]oxy]-ethyl][2-[[(2-iodo-1 1-oxo-11H-pyrido[2,1-b]quinazolin-6-yl)carbonyl]amino]ethyl], 1,1-dimethylethyl ester (0.10 g; 0.15 mmol), phenyltrimethyltin (39.8 mg; 0.17 mmol), tetrakis(triphenylphosphine)palladium (0) (17.3 mg; 0.015 mmol) and toluene (4 ml) was heated at reflux for 7 hours, cooled to room temperature, then concentrated in vacuo. The residue was purified by flash chromatography (50 g silica gel; elution with 22–28% ethyl acetate/hexane) to provide product as a yellow foam: 0.089 g.

FAB MS: m/z 617 (M$^+$+H). $^1$H NMR (300 MHz, CDCl$_3$) d 11.28(br s, 1H), 9.08(d, 1H), 8.82(d, 1H), 8.67(d, 1H), 8.20–7.72(m, 4H), 7.58–7.39(m, 3H), 7.05(t, 1H), 3.82–3.46 (m, 8H), 1.43(s, 9H), 0.87(s, 9H), 0.03(s, 6H).

EXAMPLE 26

11H-pyrido[2,1-b]quinazoline-6-carboxamide, N-[2-[(2-hydroxyethyl)amino]-ethyl]-11-oxo-2-phenyl, dihydrochloride A solution of carbamic acid, [2-[[(1,1-dimethylethyl)dimethylsilyl]oxy]ethyl][2-[[(11-oxo-2-phenyl-11H-pyrido

[2, 1-b]-quinazolin-6-yl)carbonyl]amino]ethyl], 1,1-dimethylethyl ester (0.079 g; 0.13 mmol), 6 N hydrochloric acid (0.75 ml) and methanol (4 ml) was stirred at room temperature for 7 hours, then concentrated to dryness. The residue was dissolved in ethanol (5 ml) then concentrated in vacuo to provide product as a yellow solid: 0.06 g.

FAB MS: m/z 403 (M$^+$+H). $^1$H NMR (300 MHz, CDCl$_3$) δ11.05(br s, 1H), 9.05(dd, 1H), 9.02(br s, 2H), 8.64(dd, 1H), 8.55(d, 1H), 8.35(m, 1H), 8.22(d, 1H), 7.85(m, 2H), 7.62–7.44(m, 3H), 7.25(t, 1H), 3.84(m, 2H), 3.70(m, 2H), 3.27(m, 2H), 3.10(m, 2H).

EXAMPLE 27

Carbamic acid, phenyl, 1,1-dimethylethyl ester

To a solution of aniline (5 g; 53.7 mmol) and N,N-dimethylformamide (100 ml) was added di-tert-butyl dicarbonate (11.72 g; 53.7 mmol) in one portion. The reaction mixture was stirred at room temperature for 18 hours prior to concentration in vacuo. The residue was purified by recrystallization from ethyl acetate/hexane to provide product as colorless needles: 8.56 g.

EXAMPLE 28

Carbamic acid, (2-boronophenyl), C-(1,1-dimethylethyl)ester

To a solution of carbamic acid, phenyl, 1,1-dimethylethyl ester (3.0 g; 15.5 mmol), and anhydrous tetrahydrofuran (50 ml) at −78° C., was added t-butyllithium (21.5 ml of a 1.7 M solution in pentane; 36.5 mmol) dropwise. The reaction mixture was stirred at −78° C. for 30 minutes, warmed to −20° C. for 2 hours, then cooled to −78° C. The reaction mixture was transferred by cannula to a −78° C. solution of trimethylborate (8.81 ml; 77.6 mmol) dissolved in anhydrous tetrahydrofuran (30 ml). The colorless reaction mixture was stirred at −78° C. for 45 minutes, warmed to room temperature for 15 minutes, diluted with water (200 ml) and extracted with ether (300 ml). The organic layer was washed with brine (100 ml) dried with anhydrous magnesium sulfate, filtered and concentrated in vacuo to provide the product as a pale yellow oily foam: 3.7 g.

EXAMPLE 29

Carbamic acid [2-[[[2-[2-[[(1,1-dimethylthoxy)carbonyl]amino]phenyl]-11-oxo-11H-pyrido[2,1-b]guinazolin-6-yl]carbonyl]amino]ethyl][2-[[(1,1-dimethyl-ethyl)dimethylsilyl]oxy]ethyl]-,1,1-dimethyl ester A solution of carbamic acid, [2-[[(1,1-dimethylethyl)dimethylsilyl]oxy]ethyl][2-[[(2-iodo-11-oxo-11H-pyrido[2,1-b]quinazolin-6-yl)carbonyl]amino]ethyl], 1,1-dimethylethyl ester (206 mg; 0.31 mmol), carbamic acid, (2-boronophenyl), C-(1,1-dimethylethyl) ester, (513 mg, 2.16 mmol). tetrakis(triphenylphosphine)palladium (0) (36 mg; 0.03 mmol), 2 M sodium carbonate solution (0.77 ml; 1.55 mmol) and toluene (8 ml) was heated at 120° C. for 3.5 hours, cooled to room temperature, diluted with water (50 ml) and extracted with ethyl acetate (3×25 ml). The combined organic phases were washed with brine (50 ml), dried with anhydrous magnesium sulfate, filtered and concentrated i vacuo. The residue was purified by flash chromatography on silica gel (50 g; elution with 30% ethyl acetate/hexane) to provide product as a yellow solid: 0.134 g.

FAB MS: m/z 732 (M$^+$+H). $^1$H NMR (300 MHz, CDCl$_3$) δ11.24(br s, 1H), 9.07(m, 1H), 8.85(m, 1H), 8.46(d, 1H), 8.09(m, 1H), 7.90(m, 1H), 7.42(m, 1H), 7.39–7.26(m, 2H), 7.19(m, 1H), 7.11(m, 1H), 3.82–3.62(m, 6H), 3.42–3.40(m, 2H), 1.45(s, 9H), 0.87(s, 9H), 0.03(s, 6H).

EXAMPLE 30

11H-Pyrido[2,1-b]quinazoline-6-carboxamide, 2-(2-aminophenyl)-N-[2-[(2-hydroxyethyl)amino]ethyl]-11-oxo-trihydrochloride A solution of carbamic acid [2-[[[2-[2-[[(1,1-dimethylethoxy)carbonyl]amino]phenyl]-11-oxo-11H-pyrido[2,1-b]quinazolin-6-yl]carbonyl]amino]ethyl][2-[[(1,1-dimethylethyl)dimethylsilyl]oxy]ethyl] 1,1-dimethyl ester (0.118 g; 0.16 mmol), 3N hydrochloric acid (2.3 ml) and methanol (8 ml) was stirred at room temperature for 18 hours. The reaction mixture was concentrated to dryness. The residue was dissolved in ethanol (15 ml) and concentrated to dryness several times. The product was obtained as a fine yellow solid: 84 mg.

FAB MS: m/z 418 (M$^+$+H). $^1$H NMR (300 MHz, CD$_3$OD) δ9.27(dd, 1H), 8.91(dd, 1H), 8.58(d, 1H), 8.19(d, 1H), 8.11(dd, 1H), 7.67–7.57(m, 4H), 7.44(t, 1H), 3.94(t, 2H), 3.87(t, 2H), 3.46(t, 2H), 3.28(t, 2H).

EXAMPLE 31

1,2-Benzenedicarboxyic acid, 4-bromo, 2-methyl ester and 1,2-Benzenedicarboxylic acid, 4-bromo, 1-methyl ester To methanol (20 ml) was added sodium hydride (1.0 g of a 60% mineral oil suspension; 25 mmol). After all solids were dissolved, this solution was added to a room temperature solution of 4-bromophthalic anhydride (2.27 g; 10 mmol) dissolved in methanol (50 ml). The reaction mixture was stirred at room temperature for 10 minutes, diluted with saturated potassium carbonate solution and extracted with ethyl acetate (2×). The aqueous layer was acidified to pH 1–2, then extracted with fresh ethyl acetate. These fresh organic phases were dried, filtered and concentrated in vacuo to provide a mixture of benzoic acid isomers as a waxy solid: 2.21 g.

CI MS: mlz 261 (M$^+$+H). $^1$H NMR (300 MHz, CDCl$_3$) δ11.05(br s), 8.06–7.58(m, 3H), 3.93, 3.92(2 singlets, 3H).

EXAMPLE 32

Benzoic acid, 2-amino-4-bromo, methyl ester

To a solution of 1,2-benzenedicarboxylic acid, 4-bromo, 2-methyl ester and 1,2-benzenedicarbocylic acid, 4-bromo, 1-methyl ester (2.07 g; 8 mmol), triethylamine (6.0 ml; 0.043 mol), and toluene (80 ml) was added diphenylphosphoryl azide (5.0 g; 0.018 mol). The reaction mixture was heated at 80° C. for 2 hours at which time acetone (200 ml) and water (40 ml) was added. The reaction mixture was heated further at 80° C. for 8 hours, cooled to room temperature and concentrated in vacuo. The residue was purified by flash chromatography on silica gel (elution with 15% ethyl acetate/hexane) to provide benzoic acid, 2-amino-4-bromo, methyl ester (0.514 g, as a white solid) and benzoic acid, 2-amino-5-bromo, methyl ester (0.930 g, as a white solid).

Benzoic acid, 2-amino-4-bromo, methyl ester CI MS: m/z 231 (M$^+$+H). $^1$H NMR (300 MHz, CDCl$_3$) δ7.71(d, 1H), 6.84(d, 1H), 6.74(dd, 1H), 5.80(br, 2H), 3.86(s, 3H). Benzoic acid, 2-amino-5-bromo, methyl ester CI MS: m/z 231 (M$^+$+H). $^1$H NMR (300 MHz, CDCl$_3$) δ7.94(d, 1H), 7.30 (dd, 1H), 6.57(d, 1H), 5.78(br, 2H), 3.85(s, 3H).

EXAMPLE 33

11H-Pyrido[2,1-b]quinazoline-6-carboxylic acid, 3-bromo-11-oxo

A solution of benzoic acid, 2-amino-4-bromo, methyl ester (460 mg; 2 mmol), 2-chloronicotinic acid (315 mg; 2 mmol), concentrated hydrochloric acid (5 drops), ethanol (5 ml) and water (25 ml) was heated at reflux for 18 hours, cooled to 0° C. and filtered. The solid filter cake obtained was dried in vacuo and used directly in the next Example.

EXAMPLE 34

11H-Pyrido[2,1-b]quinazoline-6-carboxamide, 3-bromo-N-[2-dimethylamino)-ethyl]-11-oxo The 11H-pyrido[2,1-b]quinazoline-6-carboxylic acid, 3-bromo-11-oxo was dissolved in dichloromethane (25 ml). To the reaction mixture was added N,N-dimethylethylenediamine (1 g; 0.011 mol), followed by the BOP reagent (1 g; 0.0023 mol). The reaction mixture was stirred at room temperature for 30 minutes, diluted with water and extracted with dichloromethane. The combined organic phases were dried, filtered and concentrated in vacuo. The residue was purified by flash chromatography on silica gel (elution with 10% methanol/chloroform) to provide product as a yellow solid: 0.338 g.

CI MS: m/z 391 (M$^+$+H). $^1$H NMR (300 MHz, CDCl$_3$) $\delta$9.04(d, 1H), 8.84(d, 1H), 8.27(d, 1H), 8.03(s, 1H), 7.60(d, 1H), 7.09(t, 1H), 3.67(q, 2H), 2.62(m, 2H), 2.41(s, 6H).

EXAMPLE 35

11H-Pyrido[2,1-b]quinazoline-6-carboxamide, 3-(3-aminophenyl)-N-[2-(dimethylamino)ethyl]-11-oxo A degassed solution of 11H-pyrido[2,1-b]quinazoline-6-carboxamide, 3-bromo-N-[2-dimethylamino)ethyl]-11-oxo (19 mg; 0.05 mmol), 3-aminophenylboronic acid (50 mg; 0.32 mmol), tetrakis(triphenylphosphine)palladium (0) (15 mg; 0.013 mmol), 2 M sodium carbonate solution (0.25 ml, 0.5 mmol) and toluene (2.5 ml) was heated at reflux for 3 hours, cooled to room temperature and concentrated to dryness. The residue was purified by flash chromatography on silica gel (elution with 50% ethyl acetate/methanol) to provide product as a yellow solid: 0.010 g.

CI MS: m/z 402 (M$^+$+H). $^1$H NMR (300 MHz, CDCl$_3$) $\delta$11.65(br s, 1H), 9.04(d, 1H), 8.81(d, 1H), 8.45(d, 1H), 7.95(s, 1H), 7.75(d, 1H), 7.31(t, 1H), 7.16(d, 1H), 7.04(m, 2H), 6.76(m, 1H), 3.84(br s, 2H), 3.74(q, 2H), 2.62(t, 2H), 2.39(s, 6H).

We claim:

1. A compound having the formula:

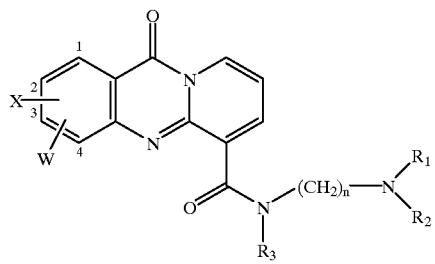

wherein:

(A) n=2–4;

(B) R$_1$ and R$_2$ are the same or different and selected from the group consisting of H, (C$_1$–C$_3$)alkyl, —CH$_2$CH$_2$OH, —CH$_2$CH$_2$NH$_2$, and —CH$_2$CH$_2$N(CH$_3$)$_2$ or R$_1$ and R$_2$ are alkyl moieties which may taken together to form a 4- to 7-membered ring;

(C) R$_3$ is selected from H, —CH$_3$, —CH$_2$CH$_3$, —CH$_2$CH$_2$NH$_2$;

(D) X is located at the 2-, or 3-position and is selected from the group consisting of 2-naphthyl, 1-naphthyl, 1-phenanthrenyl, 2-phenanthrenyl, 3-phenanthrenyl, 4-phenanthrenyl, 9-phenanthrenyl, phenyl, and mono- or polysubstituted phenyl wherein the substituents are selected from the group consisting of —OR$_4$, —NR$_5$R$_6$, (C$_1$–C$_3$) alkyl, —CF$_3$, F, Cl, Br, I, —NO$_2$, —CN, —SO$_3$H, —SO$_2$NR$_5$R$_6$, —CO$_2$H, —CO$_2$R$_4$, and phenyl;

R$_4$ is H or (C$_1$–C$_4$)alkyl;

R$_5$ and R$_6$ are the same or different and are selected from H, or (C$_1$–C$_4$)alkyl, or R$_5$ and R$_6$ are alkyl groups which may be taken together to form a 4–7 membered ring;

(E) W is selected from H, —OR$_4$, —NR$_5$R$_6$, (C$_1$–C$_3$) alkyl, —CF$_3$, F, Cl, Br, I, —NO$_2$, —CN, —SO$_2$NR$_5$R$_6$, —CO$_2$R$_4$; or a pharmaceutically acceptable salt thereof.

2. The compound according to claim 1 having the formula:

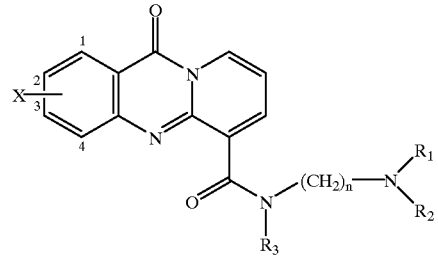

wherein:

(A) n=2–4;

(B) R$_1$ and R$_2$ are the same or different and selected from the group consisting of H, (C$_1$–C$_3$)alkyl, —CH$_2$CH$_2$OH, —CH$_2$CH$_2$NH$_2$, and —CH$_2$CH$_2$N(CH$_3$)$_2$ or R$_1$ and R$_2$ are alkyl moieties which may taken together to form a 4- to 7-membered ring;

(C) R$_3$ is selected from H, —CH$_3$, —CH$_2$CH$_3$, —CH$_2$CH$_2$NH$_2$;

(D) X is located at the 2-, or 3-position and is selected from the group consisting of 2-naphthyl, 1-naphthyl, 1-phenanthrenyl, 2-phenanthrenyl, 3-phenanthrenyl, 4-phenanthrenyl, 9-phenanthrenyl, phenyl, and mono- or polysubstituted phenyl wherein the substituents are selected from the group consisting of —OR$_4$, —NR$_5$R$_6$, (C$_1$–C$_3$) alkyl, —CF$_3$, F, Cl, Br, I, —NO$_2$, —CN, —SO$_3$H, —SO$_2$NRR$_6$, —CO$_2$H, —CO$_2$R$_4$, and phenyl;

R$_4$ is H or (C$_1$–C$_4$)alkyl;

R$_5$ and R$_6$ are the same or different and are selected from H, or (C$_1$–C$_4$)alkyl, or R$_5$ and R$_6$ are alkyl groups which may be taken together to form a 4–7 membered ring; or a pharmaceutically acceptable salt thereof.

3. The compound according to claim 1, which is 11H-pyrido[2,1-b]quinazoline-6-carboxamide, 2-(3-aminophenyl)-N-[2-(dimethylamino)ethyl]-11-oxo or a pharmaceutically acceptable salt thereof.

4. The compound according to claim 1, which is 11H-pyrido [2,1-b]quinazoline-6-carboxamide, 2-(3-aminophenyl)-N-[2-[(2-hydroxyethyl)amino]ethyl]-11-oxo-trihydrochloride.

5. The compound according to claim 1, which is 11H-pyrido[2,1-b]quinazoline-6-carboxamide, 3-(3-aminophenyl)-N-[2-(dimethylamino)ethyl]-11-oxo or a pharmaceutically acceptable salt thereof.

6. The compound according to claim 1, which is 11H-pyrido[2,1-b]quinazoline-6-carboxamide, N-[2-[(2-hydroxyethyl)amino]ethyl]-11-oxo-2-phenyl, dihydrochloride.

7. The compound according to claim 1, which is 11H-pyrido[2,1-b]quinazoline-6-carboxamide, 2-(2-aminophenyl)-N-[2-[(2-hydroxyethyl)amino]ethyl]-11-oxo-trihydrochloride.

8. The compound according to claim 1, which is 11H-pyrido[2,1-b]quiazoline-6-carboxamide,2-[1,1'biphenyl]-2-yl-N-[2-(dimethylamino)ethyl]-11-oxo or a pharmaceutically acceptable salt thereof.

9. The compound according to claim 1, which is 11H-pyrido[2,1-b]quinazoline-6-carboxamide, 2-[1,1'-biphenyl]-3-yl-N-[2-(dimethylamino)ethyl]-11-oxo or a pharmaceutically acceptable salt thereof.

10. The compound according to claim 1, which is 11H-pyrido[2,1-b]quinazoline-6-carboxamide, N-[2-(dimethylamino)ethyl-11-oxo-2-(9-phenanthrenyl) or a pharmaceutically acceptable salt thereof.

11. The compound according to claim 1, which is 11H-pyrido[2,1-b]quinazoline-6-carboxamide, N-[2-(dimethylamino)ethyl]-2-(1-naphthalenyl)-11-oxo or a pharmaceutically acceptable salt thereof.

12. The compound according to claim 1, which is 11H-pyrido[2,1-b]quinazoline-6-carboxamide, N-[2-(dimethylamino)ethyl]-11-oxo-2-[3-(trifluoromethyl)phenyl or a pharmaceutically acceptable salt thereof.

13. The compound according to claim 1, which is 11H-pyrido[2,1-b]quinazoline-6-carboxamide, N-[2-(dimethylamino)ethyl]-2-(4-methoxyphenyl)-11-oxo or a pharmaceutically acceptable salt thereof.

14. The compound according to claim 1, which is 11H-pyrido[2,1-b]quinazoline-6-carboxamide, 2-[3,5-bis(trifluoromethyl)phenyl]-N-[2-(dimethylamino)ethyl]-11-oxo or a pharmaceutically acceptable salt thereof.

15. The compound according to claim 1, which is 11H-pyrido[2,1-b]quinazoline-6-carboxamide, N-[2-(dimethylamino)ethyl]-2-[3-(dimethylamino)phenyl]-11-oxo or a pharmaceutically acceptable salt thereof.

16. A pharmaceutical composition which comprises a compound having the formula:

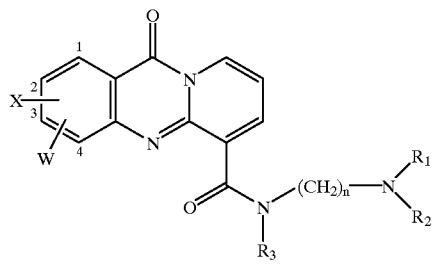

wherein:

(A) n=2–4;

(B) $R_1$ and $R_2$ are the same or different and selected from the group consisting of H, $(C_1-C_3)$alkyl, —$CH_2CH_2OH$, —$CH_2CH_2NH_2$, and —$CH_2CH_2N(CH_3)_2$ or $R_1$ and $R_2$ are alkyl moieties which may taken together to form a 4- to 7-membered ring;

(C) $R_3$ is selected from H, —$CH_3$, —$CH_2CH_3$, —$CH_2CH_2NH_2$;

(D) X is located at the 2-, or 3-position and is selected from the group consisting of 2-naphthyl, 1-naphthyl, 1-phenanthrenyl, 2-phenanthrenyl, 3-phenanthrenyl, 4-phenanthrenyl, 9-phenanthrenyl, phenyl, and mono- or polysubstituted phenyl wherein the substituents are selected from the group consisting of —$OR_4$, —$NR_5R_6$, $(C_1-C_3)$ alkyl, —$CF_3$, F, Cl, Br, I, —$NO_2$, —CN, —$SO_3H$, —$SO_2NR_5R_6$, —$CO_2H$, —$CO_2R_4$, and phenyl;

$R_4$ is H or $(C_1-C_4)$alkyl;

$R_5$ and $R_6$ are the same or different and are selected from H, or $(C_1-C_4)$alkyl, or $R_5$ and $R_6$ are alkyl groups which may be taken together to form a 4–7 membered ring;

(E) W is selected from H, —$OR_4$, —$NR_5R_6$, $(C_1-C_3)$ alkyl, —$CF_3$, F, Cl, Br, I, —$NO_2$, —CN, —$SO_2NR_5R_6$, —$CO_2R_4$; or a pharmaceutically acceptable salt thereof, and a pharmaceutical carrier.

17. A method of inhibiting growth of colon cancer in a mammal in need thereof which comprises administering to said mammal an effective amount of a compound having the formula

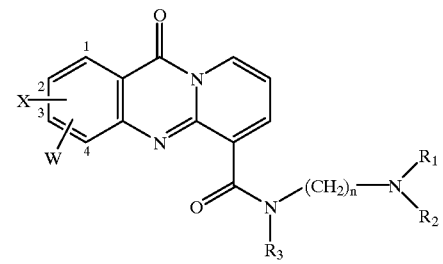

wherein:

(A) n=2–4;

(B) $R_1$ and $R_2$ are the same or different and selected from the group consisting of H, $(C_1-C_3)$alkyl, —$CH_2CH_2OH$, —$CH_2CH_2NH_2$, and —$CH_2CH_2N(CH_3)_2$ or $R_1$ and $R_2$ are alkyl moieties which may taken together to form a 4- to 7-membered ring;

(C) $R_3$ is selected from H, —$CH_3$, —$CH_2CH_3$, —$CH_2CH_2NH_2$;

(D) X is located at the 2-, or 3-position and is selected from the group consisting of 2-naphthyl, 1-naphthyl, 1-phenanthrenyl, 2-phenanthrenyl, 3-phenanthrenyl, 4-phenanthrenyl, 9-phenanthrenyl, phenyl, and mono- or polysubstituted phenyl wherein the substituents are selected from the group consisting of —$OR_4$, —$NR_5R_6$, $(C_1-C_3)$ alkyl, —$CF_3$, F, Cl, Br, I, —$NO_2$, —CN, —$SO_3H$, —$SO_2NR_5R_6$, —$CO_2H$, —$CO_2R_4$, and phenyl;

$R_4$ is H or $(C_1-C_4)$alkyl;

$R_5$ and $R_6$ are the same or different and are selected from H, or $(C_1-C_4)$alkyl, or $R_5$ and $R_6$ are alkyl groups which may be taken together to form a 4–7 membered ring;

(E) W is selected from H, —$OR_4$, —$NR_5R_6$, $(C_1-C_3)$ alkyl, —$CF_3$, F, Cl, Br, I, —$NO_2$, —CN, —$SO_2NR_5R_6$, —$CO_2R_4$; or a pharmaceutically acceptable salt thereof.

18. A method of inhibiting growth of leukemia cells in a mammal in need thereof which comprises administering to said mammal an effective amount of a compound having the formula

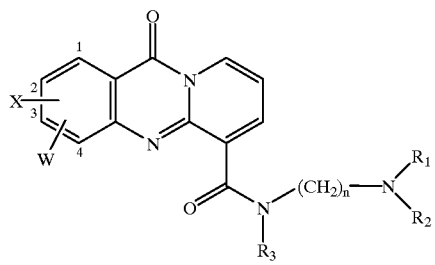

wherein:

(A) n=2–4;

(B) $R_1$ and $R_2$ are the same or different and selected from the group consisting of H, $(C_1-C_3)$alkyl, —$CH_2CH_2OH$, —$CH_2CH_2NH_2$, and —$CH_2CH_2N(CH_3)_2$ or $R_1$ and $R_2$ are alkyl moieties which may taken together to form a 4- to 7-membered ring;

(C) $R_3$ is selected from H, —$CH_3$, —$CH_2CH_3$, —$CH_2CH_2NH_2$;

(D) X is located at the 2-, or 3-position and is selected from the group consisting of 2-naphthyl, 1-naphthyl, 1-phenanthrenyl, 2-phenanthrenyl, 3-phenanthrenyl, 4-phenanthrenyl, 9-phenanthrenyl, phenyl, and mono- or polysubstituted phenyl wherein the substituents are selected from the group consisting of —$OR_4$, —$NR_5R_6$, $(C_1-C_3)$ alkyl, —$CF_3$, F, Cl, Br, I, —$NO_2$, —CN, —$SO_3H$, —$SO_2NR_5R_6$, —$CO_2H$, —$CO_2R_4$, and phenyl;

$R_4$ is H or $(C_1-C_4)$alkyl;

$R_5$ and $R_6$ are the same or different and are selected from H, or $(C_1-C_4)$alkyl, or $R_5$ and $R_6$ are alkyl groups which may be taken together to form a 4–7 membered ring;

(E) W is selected from H, —$OR_4$, —$NR_5R_6$, $(C_1-C_3)$ alkyl, —$CF_3$, F, Cl, Br, I, —$NO_2$, —CN, —$SO_2NR_5R_6$, —$CO_2R_4$; or a pharmaceutically acceptable salt thereof.

* * * * *